US009922419B2

(12) United States Patent
Takahashi

(10) Patent No.: US 9,922,419 B2
(45) Date of Patent: Mar. 20, 2018

(54) DRUG INFORMATION ACQUISITION DEVICE AND METHOD

(71) Applicant: FUJIFILM Corporation, Tokyo (JP)

(72) Inventor: Ippei Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 87 days.

(21) Appl. No.: 14/973,879

(22) Filed: Dec. 18, 2015

(65) Prior Publication Data

US 2016/0104282 A1 Apr. 14, 2016

Related U.S. Application Data

(63) Continuation of application No. PCT/JP2014/062840, filed on May 14, 2014.

(30) Foreign Application Priority Data

Jun. 19, 2013 (JP) ................................ 2013-128732

(51) Int. Cl.

*G06T 7/00* (2017.01)
*B65B 57/10* (2006.01)
*B65B 37/04* (2006.01)
*B65B 5/10* (2006.01)

(Continued)

(52) U.S. Cl.

CPC ............ *G06T 7/0012* (2013.01); *B65B 5/103* (2013.01); *B65B 37/04* (2013.01); *G01N 21/251* (2013.01);

(Continued)

(58) Field of Classification Search

CPC . A61J 1/00; B65B 37/04; B65B 57/10; B65B 5/103; G01N 21/251;

(Continued)

(56) References Cited

U.S. PATENT DOCUMENTS

2005/0217208 A1 10/2005 Cicognani
2009/0255948 A1* 10/2009 Bassani .................. B65B 5/103
221/1

(Continued)

FOREIGN PATENT DOCUMENTS

JP 7-200770 A 8/1995
JP 8-322913 A 12/1996

(Continued)

OTHER PUBLICATIONS

Communication dated May 4, 2016, issued by the European Patent Office in corresponding European Application No. 14813551.0.
International Search Report for PCT/JP2014/062840 dated Jun. 17, 2014 [PCT/ISA/210].
Written Opinion for PCT/JP2014/062840 dated Jun. 17, 2014 [PCT/ISA/237].

*Primary Examiner* — Kenny Cese
(74) *Attorney, Agent, or Firm* — Sughrue Mion, PLLC

(57) ABSTRACT

A row of V-shaped grooves is formed in the bottom of each of imaging trays which temporarily hold a dose of drug. After drugs are inserted into the imaging tray, the imaging tray is vibrated to remove the overlap between the drugs corresponding to a dose and to correct the posture of the drugs using a first inclined surface and a second inclined surface of the V-shaped groove. Two cameras are provided so as to face the first inclined surface and the second inclined surface of the V-shaped groove, respectively, and capture the images of the drugs which have stable postures that have been corrected on the V-shaped grooves, in two directions. The first and second images of the drugs captured in two directions are processed to accurately acquire drug information including at least outward appearance information of the drugs.

16 Claims, 20 Drawing Sheets

(51) Int. Cl.

| | |
|---|---|
| ***G01N 21/25*** | (2006.01) |
| ***H04N 9/04*** | (2006.01) |
| ***G06T 7/90*** | (2017.01) |
| *G01N 21/95* | (2006.01) |
| *A61J 1/00* | (2006.01) |

(52) U.S. Cl.
CPC ................. *G06T 7/90* (2017.01); *H04N 9/04* (2013.01); *A61J 1/00* (2013.01); *B65B 57/10* (2013.01); *G01N 21/9508* (2013.01); *G06T 2207/10024* (2013.01); *G06T 2210/41* (2013.01)

(58) Field of Classification Search
CPC ...... G01N 21/9508; G06T 2207/10024; G06T 7/90; G06T 7/0012; G06T 2210/41; H04N 9/04
See application file for complete search history.

(56) References Cited

U.S. PATENT DOCUMENTS

| | | | | |
|---|---|---|---|---|
| 2012/0216485 | A1 | 8/2012 | Amano et al. | |
| 2013/0279774 | A1* | 10/2013 | Helgason .............. | A61J 7/0084 382/128 |
| 2013/0342676 | A1* | 12/2013 | Amano .................... | H04N 7/18 348/86 |

FOREIGN PATENT DOCUMENTS

| | | | |
|---|---|---|---|
| JP | 2005-525973 | A | 9/2005 |
| JP | 2011-104077 | A | 6/2011 |
| WO | 2011/062101 | A1 | 5/2011 |
| WO | 2012/147907 | A1 | 11/2012 |

* cited by examiner (a)

(b)

(a)

(b)

(a)

(b)

DRUG INFORMATION ACQUISITION DEVICE AND METHOD

CROSS-REFERENCE TO RELATED APPLICATIONS

The present application is a Continuation of PCT International Application No. PCT/JP2014/062840 filed on May 14, 2014 claiming priority under 35 U.S.C §119(a) to Japanese Patent Application No. 2013-128732 filed on Jun. 19, 2013. Each of the above applications is hereby expressly incorporated by reference, in their entirety, into the present application.

BACKGROUND OF THE INVENTION

1. Field of the Invention

The present invention relates to a drug information acquisition device and method, and more particularly, to a technique for acquiring information, such as the type and number of drugs to be packaged, immediately before a packaging apparatus automatically packages each dose of a plurality of types of drugs.

2. Description of the Related Art

A system has been proposed which inserts each dose of drugs (pills) to a transparent packet, captures the image of the drugs from the upper side of the packet, and performs an image recognition process for the captured image to calculate the number of drugs in the packet (JP1995-200770A (JP-H07-200770A)).

This system can capture the image of the drugs inserted to the packet and process the captured image to calculate the number of drugs. However, in the determination of the type of drug, it is difficult to remove the overlap between the drugs in the packet or to solve problems caused by the orientation (lateral direction) of the drugs. In addition, in some cases, characters are printed on the packet or light is randomly reflected from the packet. For these reasons, it is difficult to technically achieve the system.

In order to solve the above-mentioned problems, a drug dispensing device has been proposed which places drugs to be dispensed on a drug inspection table, vibrates the drug inspection table in the horizontal direction to remove the overlap between the drugs, captures the image of the drugs on the drug inspection table while vibrating the drug inspection table, and performs an image recognition process to calculate the number of drugs on the basis of the captured image, immediately before automatically dispensing each dose of drugs (JP2011-104077A). In addition, a plurality of grooves which are partitioned by convex portions extending in a vibration direction are formed in the bottom of the drug inspection table described in JP2011-104077A and the drugs are guided by the grooves and are smoothly dispersed on the drug inspection table.

JP2005-525973A discloses a device which fills a bottle with the same type of drug (pill). This device includes first conveying means which is provided between a hopper storing a large number of drugs and a bottle, includes a plurality of inclined vibration plates arranged in a line, and vibrates each vibration plate to convey the drugs on the vibration plates, second conveying means which is a drum that is provided in an exit portion of the vibration plate and is rotated while drawing the drugs, and a camera which captures the image of the drugs on the drum in order to count the number of drugs. A groove is formed in the bottom of each vibration plate in the conveyance direction. Therefore, it is possible to convey the drugs in a line along the groove.

In addition, JP2005-525973A discloses a structure in which the groove formed in the bottom of the vibration plate and a plurality of grooves formed in a circumferential surface of the drum have a triangular shape (V-shape).

SUMMARY OF THE INVENTION

The drug dispensing device disclosed in JP2011-104077A places the drugs on the drug inspection table and vibrates the drug inspection table to remove the overlap between the drugs, immediately before dispensing the drugs. Therefore, it is possible to more accurately count the number of drugs, using the image recognition process, as compared to the structure disclosed in JP1995-200770A (JP-H07-200770A).

However, the drug dispensing device disclosed in JP2011-104077A counts the number of drugs corresponding to a dose, but does not recognize the type of drug. Therefore, it is difficult for the drug dispensing device to accurately recognize whether a dose of drug is dispensed according to a prescription.

For example, in a stage in which a dose of drug is prepared, a manual distribution operation which sequentially puts a dose of drug in each of the containers (measures) which are partitioned in a grid is performed. However, when some drugs are exchanged between adjacent containers, the number of drugs corresponding to a dose is correct, but a combination of the drugs is not correct. Since the drug dispensing device disclosed in JP2011-104077A does not recognize the type of drug, it is difficult for the drug dispensing device to recognize the exchange between the drugs.

However, JP2011-104077A discloses a structure which extracts the contour of the drug using the image recognition process. It is possible to vibrate the drug inspection table to remove the overlap between the drugs. However, in the case of drugs with various three-dimensional shapes, when the drugs are adjacent to each other, the contours of the drugs overlap each other in the captured image, which makes it difficult to accurately acquire the outward appearances (contours) of all of the drugs. In addition, a drug with a flat side surface is stable in two states, that is, a state in which the upper surface or lower surface of the drug comes into contact with the bottom of the drug inspection table and a state in which the side surface of the drug comes into contact with the bottom of the drug inspection table. Therefore, in some cases, the posture of the drug is not changed even though the drug inspection table is vibrated. The camera which is provided in the drug dispensing device disclosed in JP2011-104077A captures the image of the entire bottom of the drug inspection table from the upper side. Therefore, in some cases, the camera captures only the image of the upper surface or lower surface of the drug or only the image of the side surface of the drug. In this case, an error in the determination of the outward appearance of the drug is likely to occur.

JP2005-525973A discloses the structure in which the groove formed in the bottom of the vibration plate for conveying drugs and a plurality of grooves formed in the circumferential surface of the drum have a triangular shape and the posture of the drug is corrected by two lateral walls of the triangular groove. The camera captures the image of the drugs drawn to the drum in a direction facing the side surface of the drum. Therefore, in the case of a disc-shaped drug, the camera captures the image of the drug in an oblique direction. As a result, it is difficult for the camera to capture only the image of the upper surface or lower surface of the drug.

The invention has been made in view of the above-mentioned problems and an object of the invention is to provide a drug information acquisition device and method which can accurately detect the outward appearance of drugs with various shapes and accurately acquire drug information including at least the outward appearance information of a dose of drug.

In order to achieve the object, according to an aspect of the invention, there is provided a drug information acquisition device including: an imaging tray that is provided between a drug supply unit which sequentially supplies each dose of a plurality of types of drugs and a packet insertion guide, temporarily holds a dose of drug supplied from the drug supply unit, and has a bottom in which a row of V-shaped grooves, each having a first inclined surface and a second inclined surface, is formed; a mechanical unit that removes an overlap between the drugs corresponding to a dose supplied to the imaging tray and corrects the posture of the drugs using the first inclined surface and the second inclined surface of the V-shaped groove; an illumination unit that illuminates the drugs on the imaging tray; first and second imaging units that are provided so as to face the first inclined surface and the second inclined surface in the bottom of the imaging tray, respectively, and capture images of the drugs, whose posture is corrected by the mechanical unit and which are illuminated by the illumination unit, on the imaging tray; and a drug information acquisition unit that processes a first image and a second image which are respectively acquired from the first imaging unit and the second imaging unit to acquire drug information including at least outward appearance information of the drugs in the first image and the second image.

According to the above-mentioned aspect of the invention, a row of V-shaped grooves is formed in the bottom of the imaging tray which temporarily holds a dose of drug to remove the overlap between the drugs corresponding to a dose supplied from the drug supply unit to the imaging tray and the posture of the drug is corrected by the first inclined surface and the second inclined surface of the V-shaped groove. That is, the drug is stably held along the first inclined surface and the second inclined surface of the V-shaped groove, according to the shape of the drug. As a result, the drug has a posture suitable for imaging. The first imaging unit and the second imaging unit are provided so as to face the first inclined surface and the second inclined surface of the V-shaped groove, respectively, and can capture the image of the drug which has a stable posture which has been corrected on the V-shaped groove in two directions (a front direction and a lateral direction). Therefore, the first image and the second image of the drug captured in two directions can be processed to accurately acquire drug information including at least the outward appearance information of the drug.

In the drug information acquisition device according to another aspect of the invention, it is preferable that the mechanical unit is a vibration unit that vibrates the imaging tray.

In the drug information acquisition device according to yet another aspect of the invention, it is preferable that the first inclined surface and the second inclined surface of the V-shaped groove have the same inclination angle and an angle formed between the first inclined surface and the second inclined surface is equal to or greater than 60 degrees and equal to or less than 150 degrees. The reason for this is that, when the angle formed between the first inclined surface and the second inclined surface is in the range of 60 degrees or higher and 150 degrees or less, the effect of adjusting the posture of the drug is reduced. When the angle formed between the first inclined surface and the second inclined surface is within the range of 60 degrees or higher and 150 degrees or less, the angle formed between the optical axes of the first imaging unit and the second imaging unit is slightly less than the angle of the V-shaped groove such that a portion of the drug is not hidden by the first inclined surface or the second inclined surface during image capture.

In the drug information acquisition device according to yet another aspect of the invention, it is preferable that the first inclined surface and the second inclined surface of the V-shaped groove have different inclination angles and an angle formed between the first inclined surface and the second inclined surface is equal to or greater than 60 degrees and equal to or less than 150 degrees.

In the drug information acquisition device according to yet another aspect of the invention, it is preferable that the drug information acquisition unit includes a storage unit that stores size correction information corresponding to an object distance of each V-shaped groove in the row of the V-shaped grooves in the bottom of the imaging tray, reads the corresponding size correction information from the storage unit according to which of the V-shaped grooves in the row of the V-shaped grooves of the imaging tray the drug is located in, and corrects size information which is included in the outward appearance information acquired by the image processing with the read size correction information.

The object distance from the first imaging unit or the second imaging unit to the drug varies depending on the V-shaped groove in the row of V-shaped grooves in the bottom of the imaging tray. Therefore, the corresponding size correction information is read from the storage unit according to which of the V-shaped grooves in the row of the V-shaped grooves of the imaging tray the drug is located in and the size information which is included in the outward appearance information acquired by the image processing is corrected with the read size correction information. That is, it is possible to acquire the drug information including the same size information from the same drug, regardless of which of the V-shaped grooves in the row of the V-shaped grooves of the imaging tray the drug is located in.

In the drug information acquisition device according to yet another aspect of the invention, it is preferable that a plurality of the imaging trays are provided. In addition, it is preferable that the drug information acquisition device further includes: a moving mechanism that moves the plurality of imaging trays between at least two of a position where the drug is supplied from the drug supply unit to the imaging tray, a position where the vibration unit vibrates the imaging tray, a position where the first imaging unit and the second imaging unit capture the image of the drug in the imaging tray, and a position where the drug is discharged from the imaging tray to the packet insertion guide after the image capture; and a control unit that simultaneously operates the plurality of imaging trays at the two or more positions.

According to the above-mentioned structure, it is possible to substantially increase a processing speed and to prevent a reduction in the packaging speed of the packaging apparatus, as compared to a case in which a series of operations of receiving a dose of drug, vibrating the imaging tray, capturing the image of the drugs in the imaging tray, and discharging the drugs in the imaging tray to the packet insertion guide is performed in only one imaging tray.

In the drug information acquisition device according to yet another aspect of the invention, the first imaging unit and the second imaging unit are provided in an obliquely upward direction with respect to the imaging tray.

Preferably, the drug information acquisition device according to yet another aspect of the invention further includes: an image acquisition unit that instructs at least one of the first imaging unit and the second imaging unit to continuously capture the image of the drug on the imaging tray while the vibration unit is vibrating the imaging tray and acquires a continuous image; a determination unit that determines whether the overlap between the drugs corresponding to a dose supplied to the imaging tray has been removed and whether the posture of the drugs has been corrected, on the basis of the image acquired by the image acquisition unit; and a control unit that stops the vibration of the imaging tray by the vibration unit when the determination unit determines that the overlap between the drugs has been removed and that the posture of the drugs has been corrected. It is preferable that the drug information acquisition unit acquires the drug information on the basis of the first image and the second image which are acquired from the first imaging unit and the second imaging unit, respectively, after the vibration of the imaging tray is stopped. According to this structure, it is possible to stop vibration at the time when it is determined that the overlap between the drugs has been removed and thus to shorten the vibration time. The resolution of the image which is captured during vibration is reduced by the influence of image blurring. However, the quality of the image is sufficient to determine the overlap between the drugs.

In the drug information acquisition device according to yet another aspect of the invention, at least the bottom of the imaging tray is a transparent member, and the first imaging unit and the second imaging unit are provided in an obliquely downward direction with respect to the imaging tray and capture the image of the drug through the transparent member. According to this structure, it is possible to increase flexibility in the arrangement of the first imaging unit and the second imaging unit.

In the drug information acquisition device according to yet another aspect of the invention, it is preferable that at least the bottom of the imaging tray is a transparent member. It is preferable that the drug information acquisition device further includes third and fourth imaging units that are provided so as to face the first imaging unit and the second imaging unit, respectively, with the imaging tray interposed therebetween, and capture images of the drugs through the transparent member. It is preferable that the drug information acquisition unit processes each of first to fourth images acquired by the first to fourth imaging units to acquire drug information including at least outward appearance information of the drugs in the first to fourth images.

According to the above-mentioned structure, it is possible to capture the image of the drugs in four directions. When character information is printed or stamped on a drug or when a secant line is engraved in the drug, it is possible to reliably capture the image of the character information or the secant line.

In the drug information acquisition device according to yet another aspect of the invention, it is preferable that the drug information acquisition unit further acquires at least one of color information, character information, and a secant line of the drug in the image, using the image processing.

According to another aspect of the invention, there is provided a drug information acquisition method that is performed in a drug information acquisition device including an imaging tray that is provided between a drug supply unit and a packet insertion guide and has a bottom in which a row of V-shaped grooves, each having a first inclined surface and a second inclined surface, is formed, a vibration unit that vibrates the imaging tray, an illumination unit that illuminates drugs on the imaging tray, first and second imaging units that are provided so as to face the first inclined surface and the second inclined surface in the bottom of the imaging tray, respectively, and a drug information acquisition unit. The method includes: a drug supply step of supplying each dose of a plurality of types of drugs from the drug supply unit to the imaging tray; a vibration step of vibrating the imaging tray with the vibration unit to remove an overlap between the drugs corresponding to a dose supplied to the imaging tray and to correct the posture of the drugs using the first inclined surface and the second inclined surface of the V-shaped groove; an imaging step of capturing images of the drugs on the imaging tray illuminated by the illumination unit, using the first imaging unit and the second imaging unit, to acquire a first image and a second image after the vibration step; and a drug information acquisition step of processing the first image and the second image acquired in the imaging step, using the drug information acquisition unit, to acquire drug information including at least outward appearance information of the drugs in the first image and the second image.

According to still another aspect of the invention, there is provided a drug information acquisition method that is performed in a drug information acquisition device including an imaging tray that is provided between a drug supply unit and a packet insertion guide and has a bottom in which a row of V-shaped grooves, each having a first inclined surface and a second inclined surface, is formed, a vibration unit that vibrates the imaging tray, an illumination unit that illuminates drugs on the imaging tray, first and second imaging units that are provided so as to face the first inclined surface and the second inclined surface in the bottom of the imaging tray, respectively, and a drug information acquisition unit. The method includes: a drug supply step of supplying each dose of a plurality of types of drugs from the drug supply unit to the imaging tray; a vibration step of vibrating the imaging tray with the vibration unit to remove an overlap between the drugs corresponding to a dose supplied to the imaging tray and to correct the posture of the drugs using the first inclined surface and the second inclined surface of the V-shaped groove; a first imaging step of continuously capturing images of the drugs on the imaging tray illuminated by the illumination unit, using at least one of the first imaging unit and the second imaging unit, to acquire a continuous image during the vibration of the imaging tray in the vibration step; a determination step of determining whether the overlap between the drugs corresponding to a dose supplied to the imaging tray has been removed and whether the posture of the drugs has been corrected, on the basis of the image acquired in the first imaging step; a step of stopping the vibration of the imaging tray in the vibration step when it is determined in the determination step that the overlap between the drugs has been removed and the posture of the drugs has been corrected; a second imaging step of capturing images of the drugs on the imaging tray illuminated by the illumination unit, using the first imaging unit and the second imaging unit, to acquire a first image and a second image after the vibration of the imaging tray is stopped; and a drug information acquisition step of processing the first image and the second image acquired in the second imaging step, using the drug information acquisition unit, to acquire drug information including at least outward appearance information of the drugs in the first image and the second image.

According to the invention, the image of the drug whose posture as been adjusted is captured in at least two directions. Therefore, it is possible to accurately detect the outward appearance of drugs with various shapes and to accurately acquire drug information including at least the outward appearance information of a dose of drug.

Figure 6:
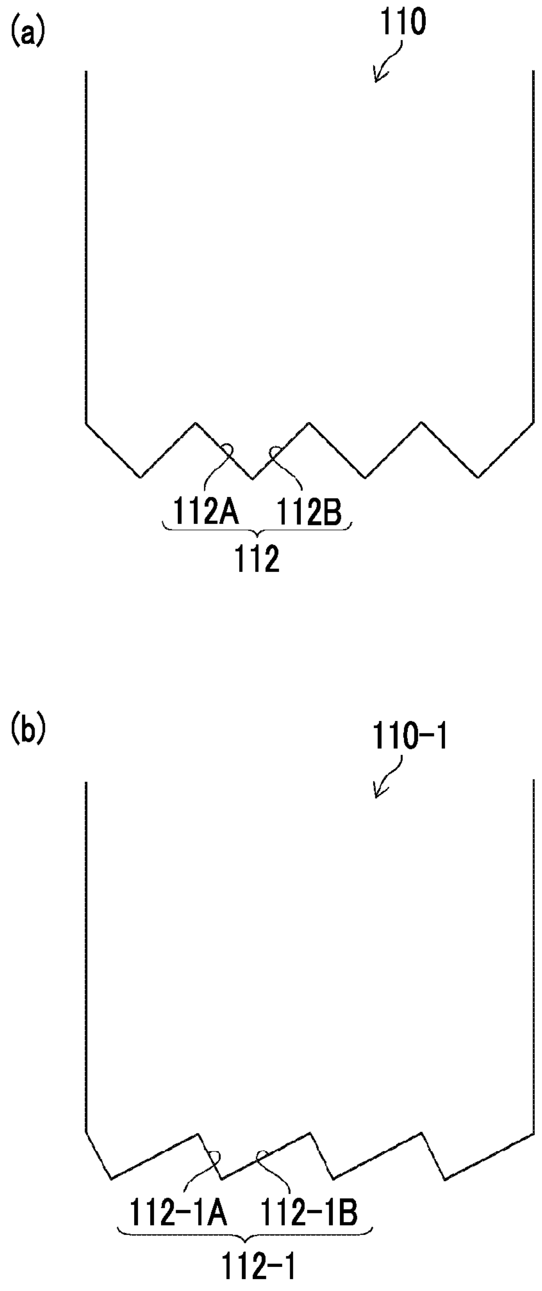

(a) and (b) of FIG. 6 are diagrams illustrating the shape of the bottom of the imaging tray.

Figure 7:
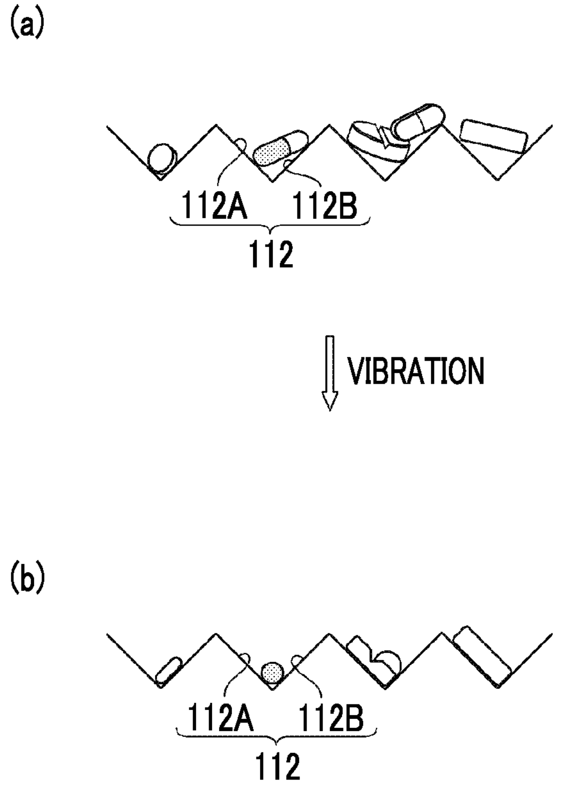

(a) and (b) of FIG. 7 are diagrams illustrating the state of drugs before and after the imaging tray is vibrated, respectively.

Figure 3:
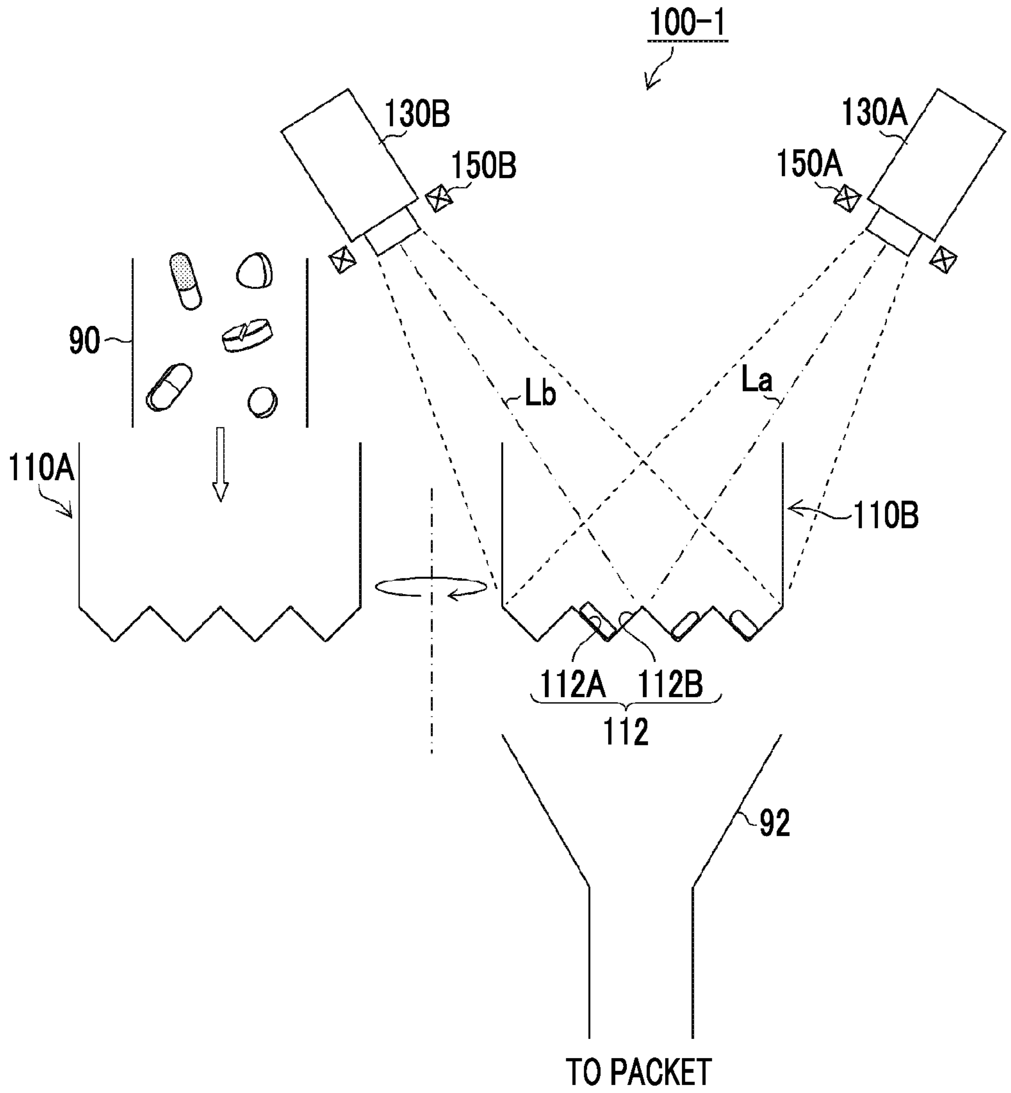
FIG. 3 is a diagram schematically illustrating a main portion of a first embodiment of the drug information acquisition device according to the invention.
Figure 8:
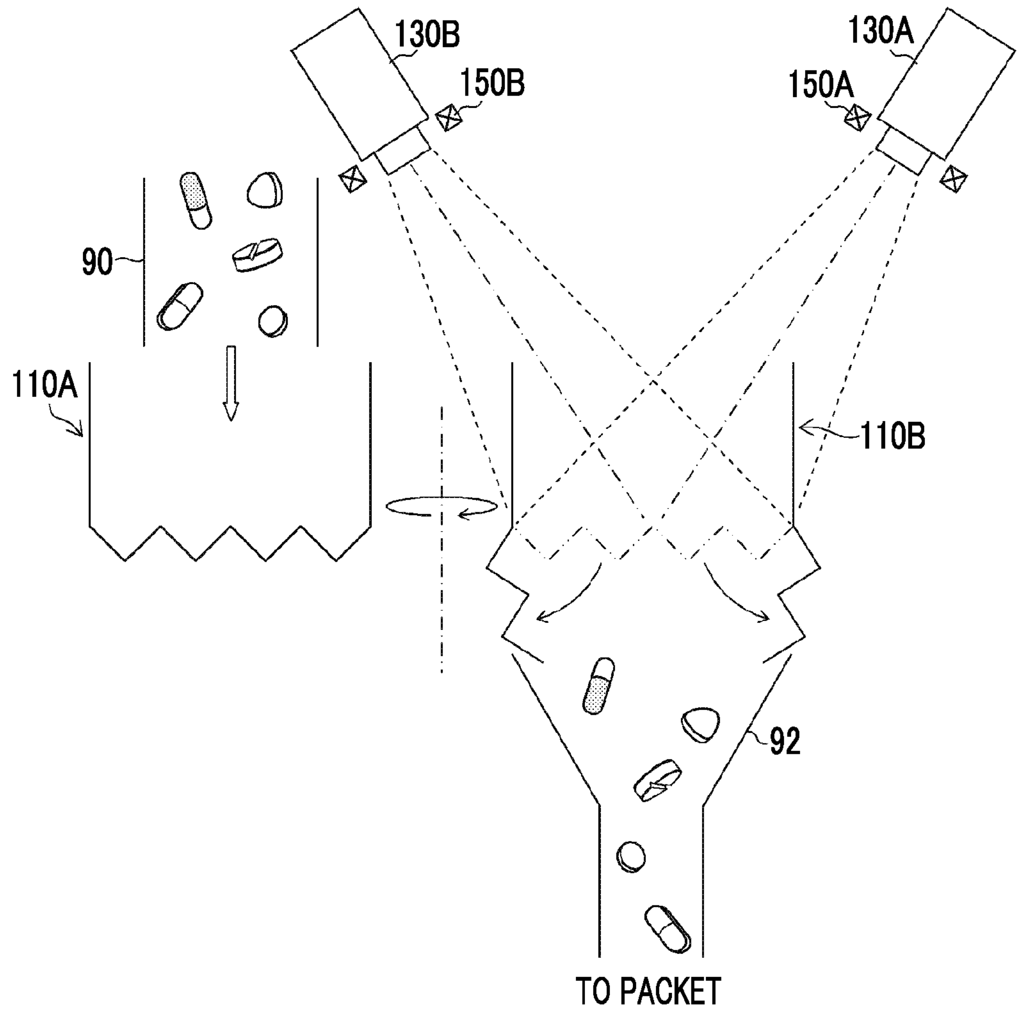

FIG. 8 is a diagram illustrating an aspect in which the drugs are discharged from the imaging tray in the drug information acquisition device according to the first embodiment illustrated in FIG. 3.

Figure 9:
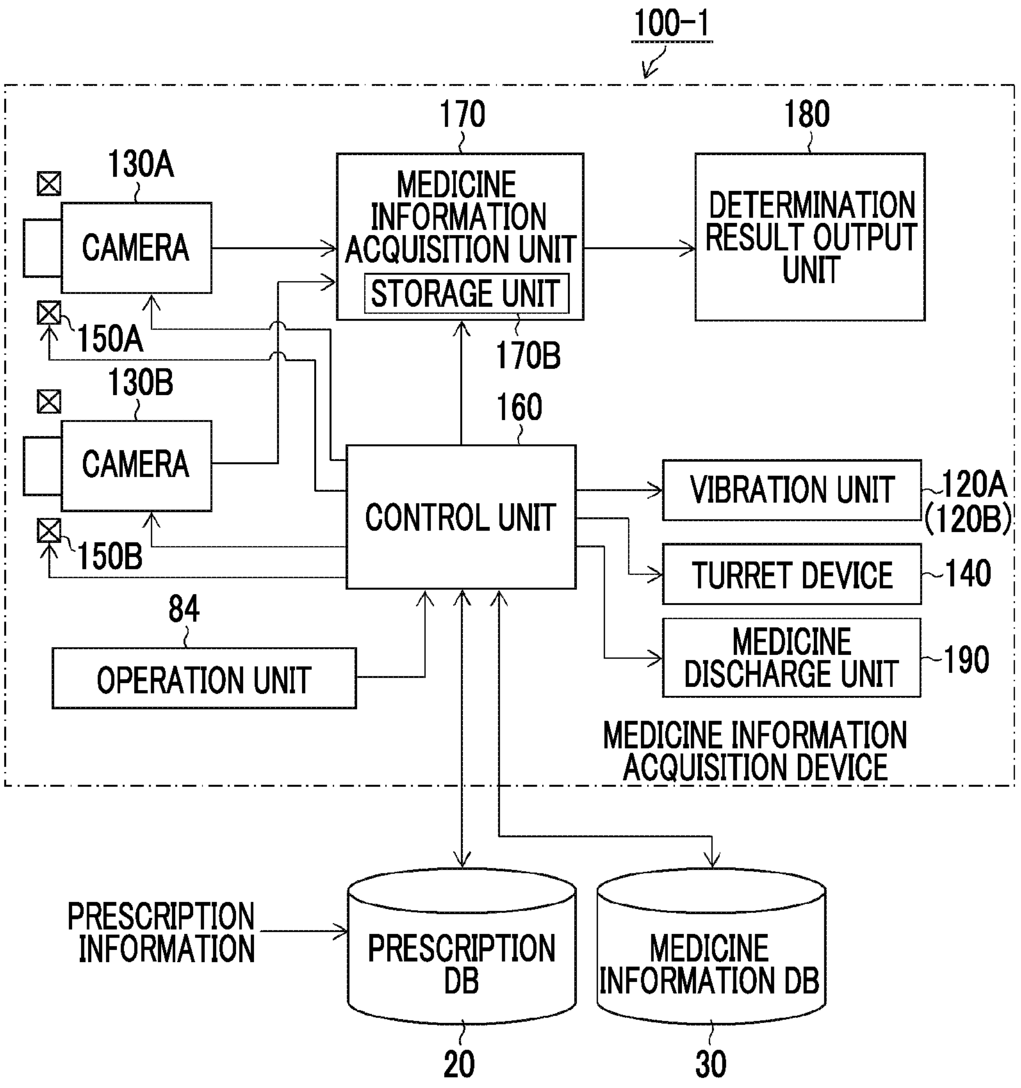

FIG. 9 is a block diagram illustrating an embodiment of the internal structure of the drug information acquisition device.

Figure 10:
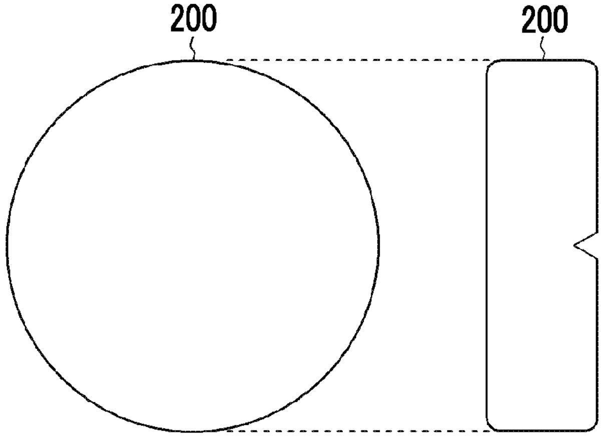
Figure 10:
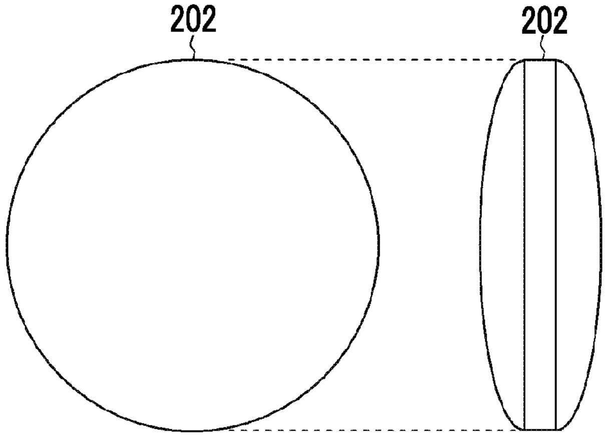

(a) and (b) of FIG. 10 are diagrams illustrating drugs with different side shapes.

Figure 11:
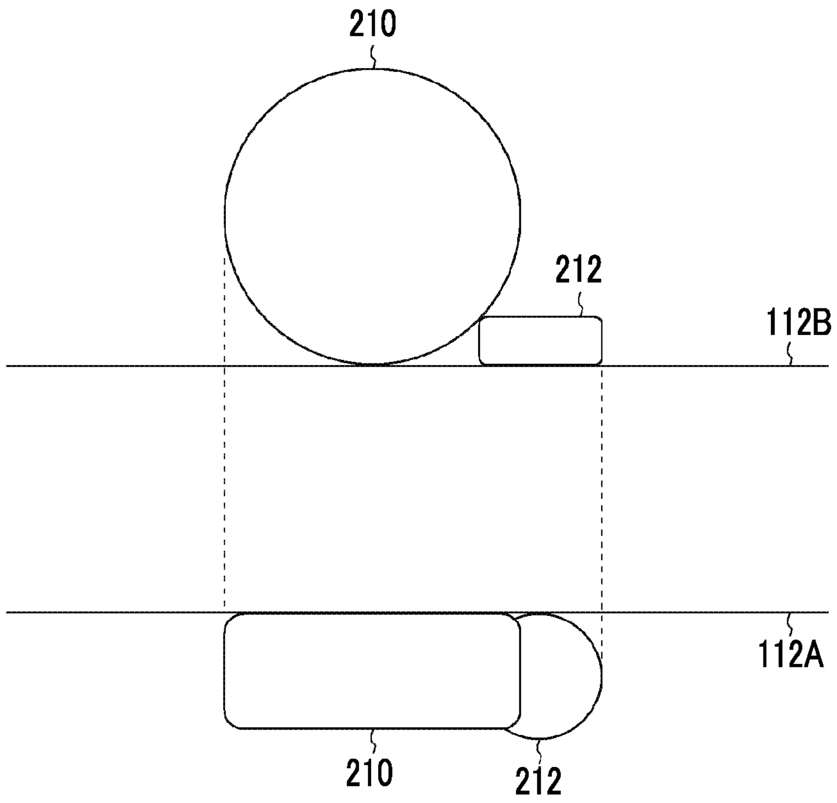

(a) and (b) of FIG. 11 are diagrams illustrating an example of two images which are captured in a direction perpendicular to a first inclined surface of a V-shaped groove in the bottom of the imaging tray and a direction perpendicular to a second inclined surface of the V-shaped groove, respectively.

Figure 12:
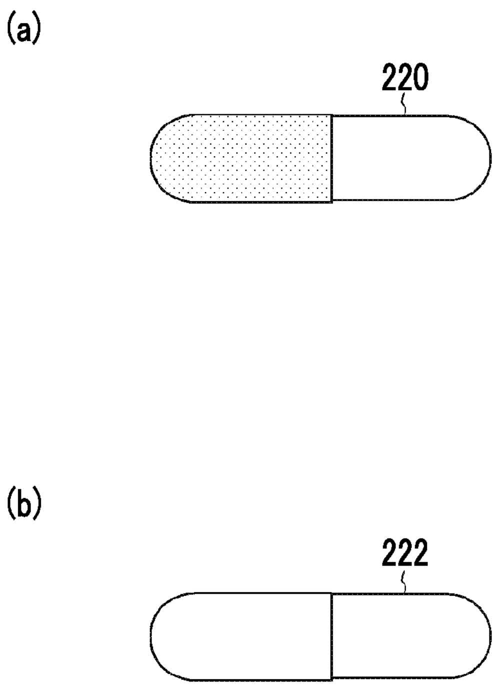

(a) and (b) of FIG. 12 are diagrams illustrating an example of drugs which have the same shape and different colors.

Figure 13:
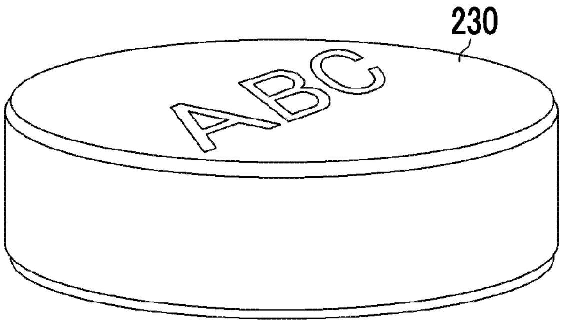
Figure 13:
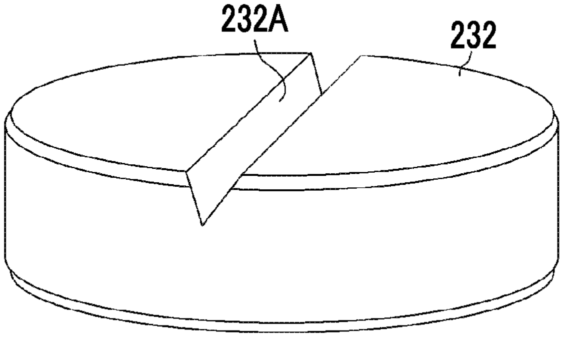

(a) and (b) of FIG. 13 are diagrams illustrating a drug having characters printed or stamped on the surface thereof and a drug having a secant line formed therein, respectively.

Figure 14:
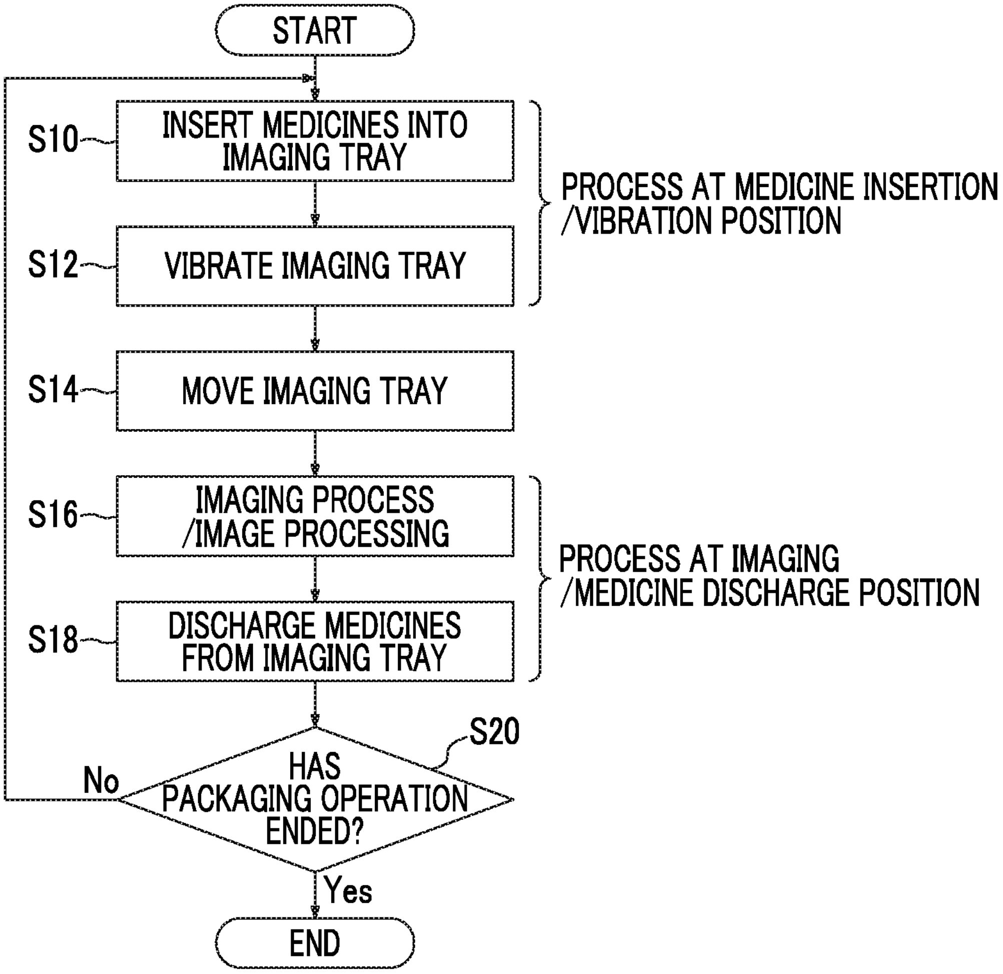

FIG. 14 is a flowchart illustrating the procedure of a process of the drug information acquisition device according to the first embodiment.

Figure 15:
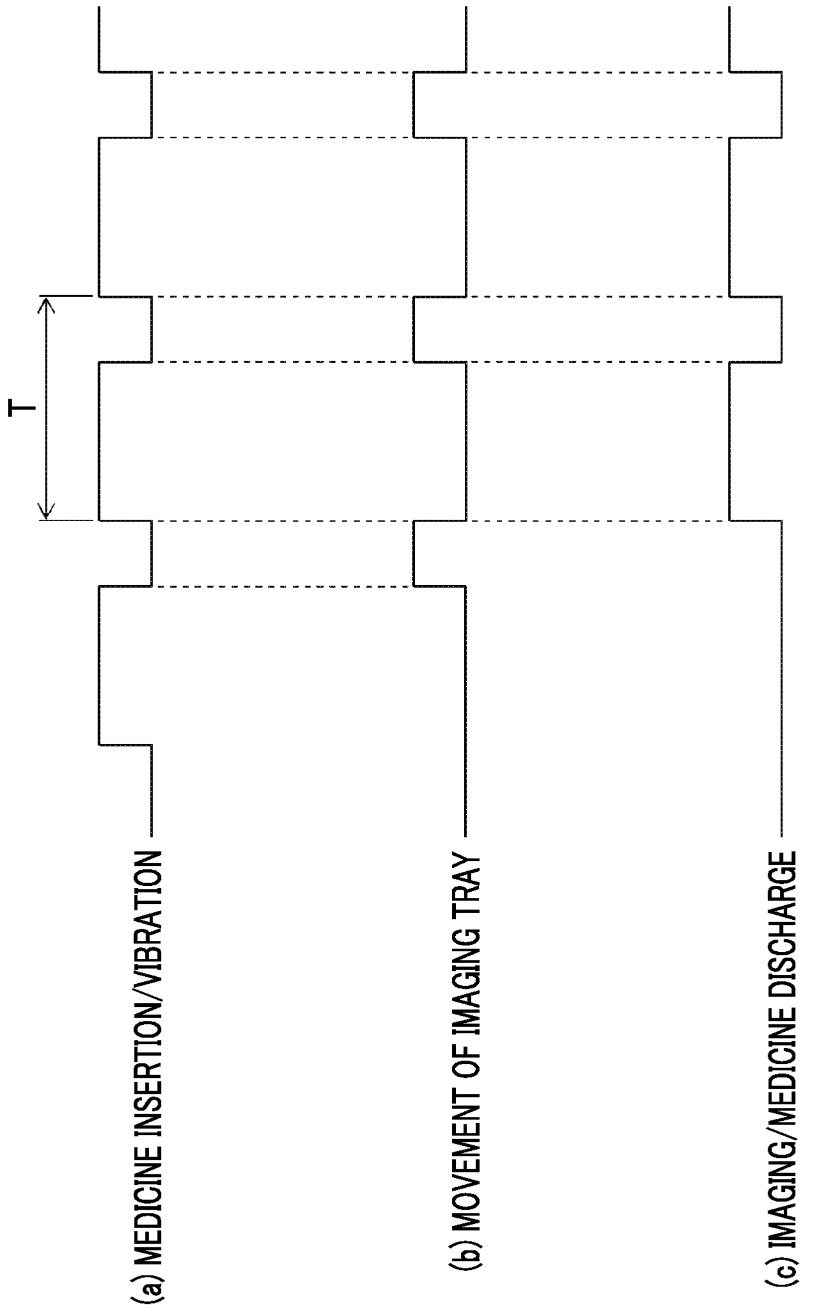

FIG. 15 is a timing chart illustrating the procedure of the process of the drug information acquisition device at a drug insertion/vibration position and an imaging/drug discharge position.

Figure 16:
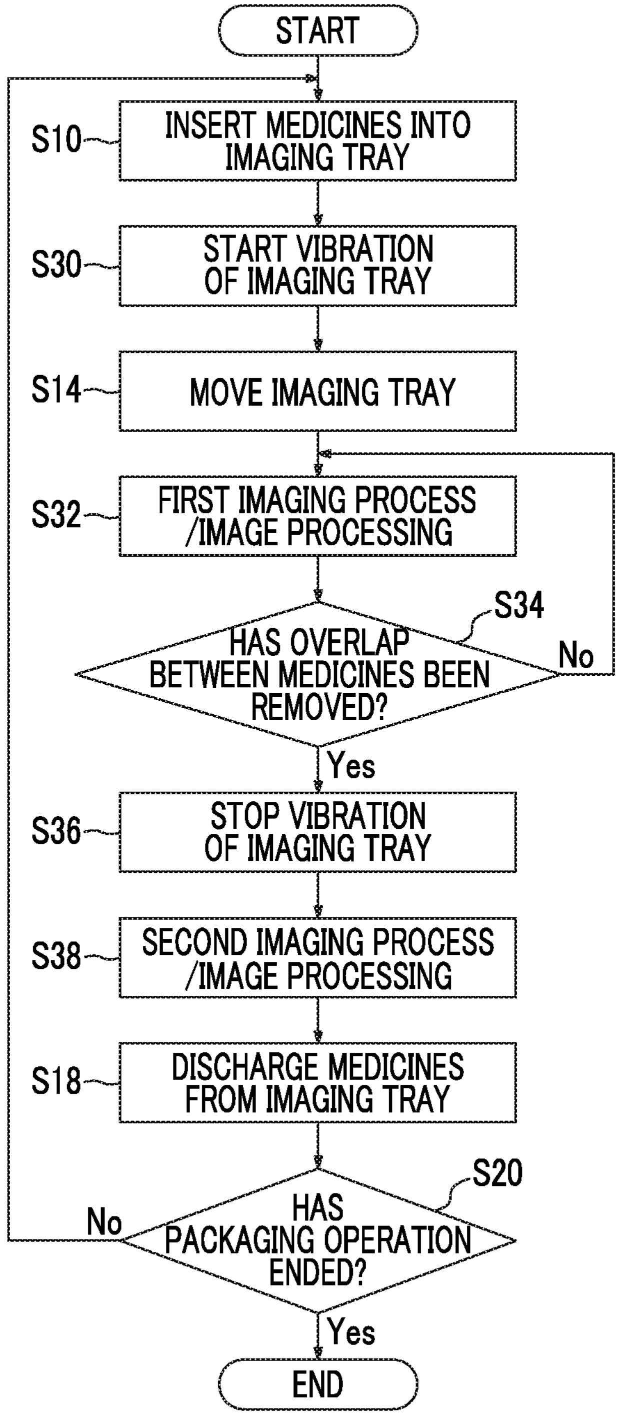

FIG. 16 is a flowchart illustrating the procedure of a process of a drug information acquisition device according to a modification example of the first embodiment.

Figure 17:
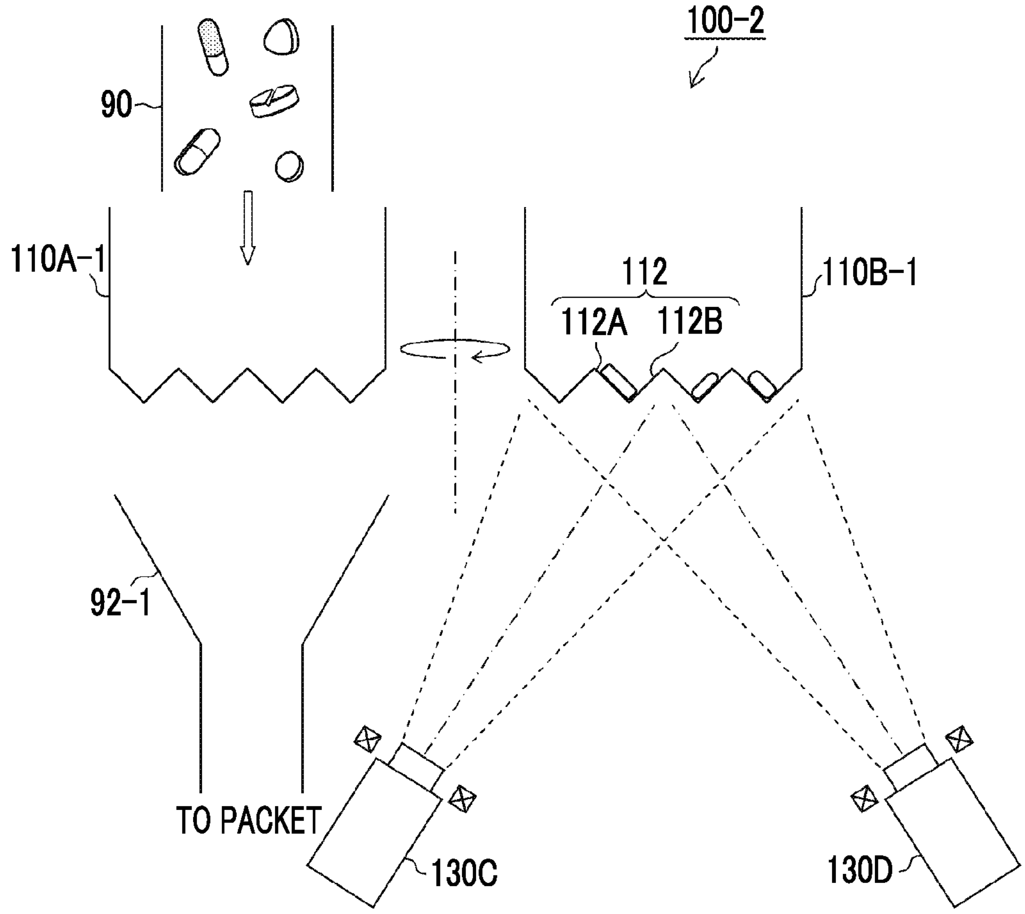

FIG. 17 is a diagram schematically illustrating a main portion of a second embodiment of the drug information acquisition device according to the invention.

Figure 18:
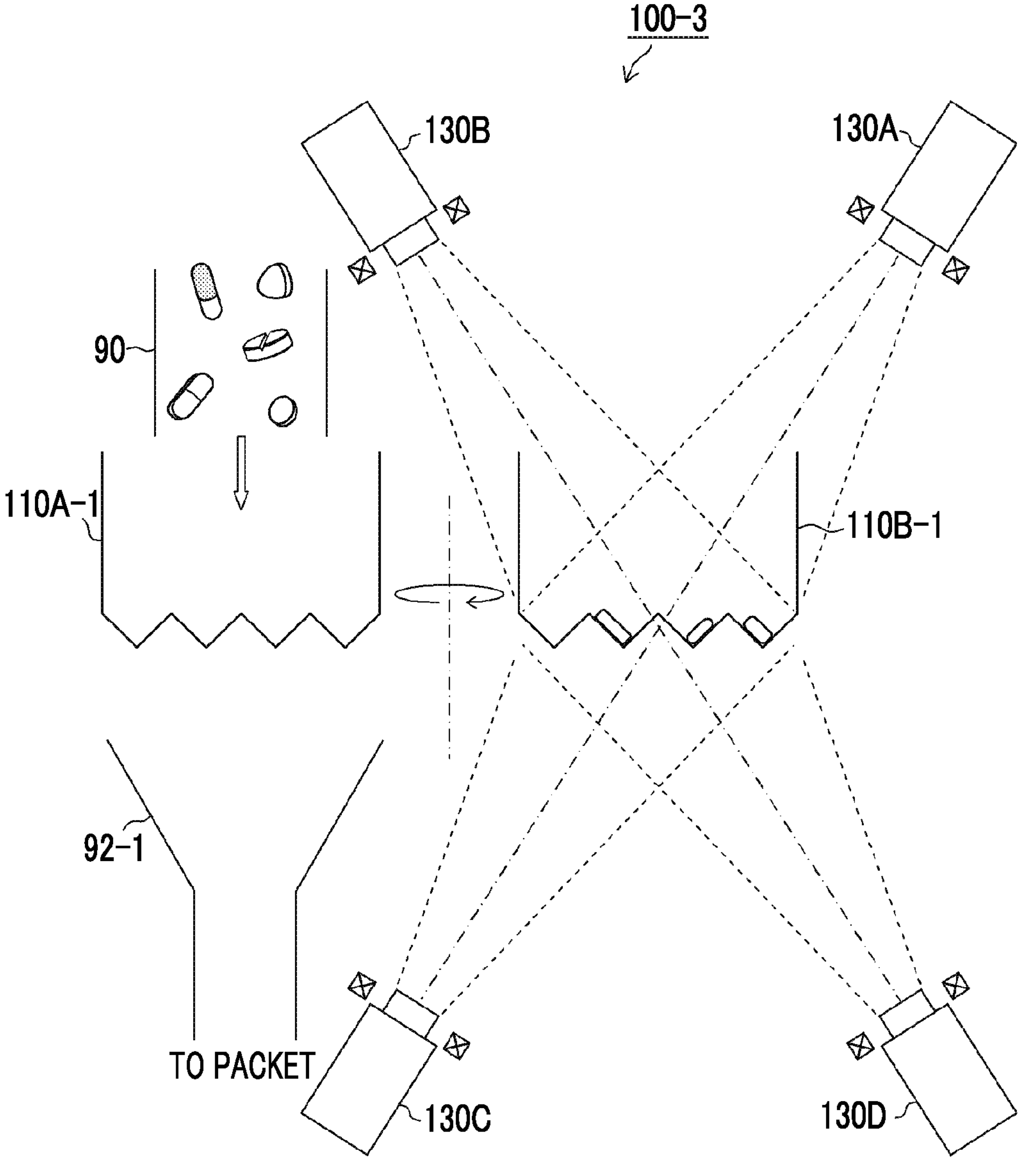

FIG. 18 is a diagram schematically illustrating a main portion of a third embodiment of the drug information acquisition device according to the invention.

Figure 19:
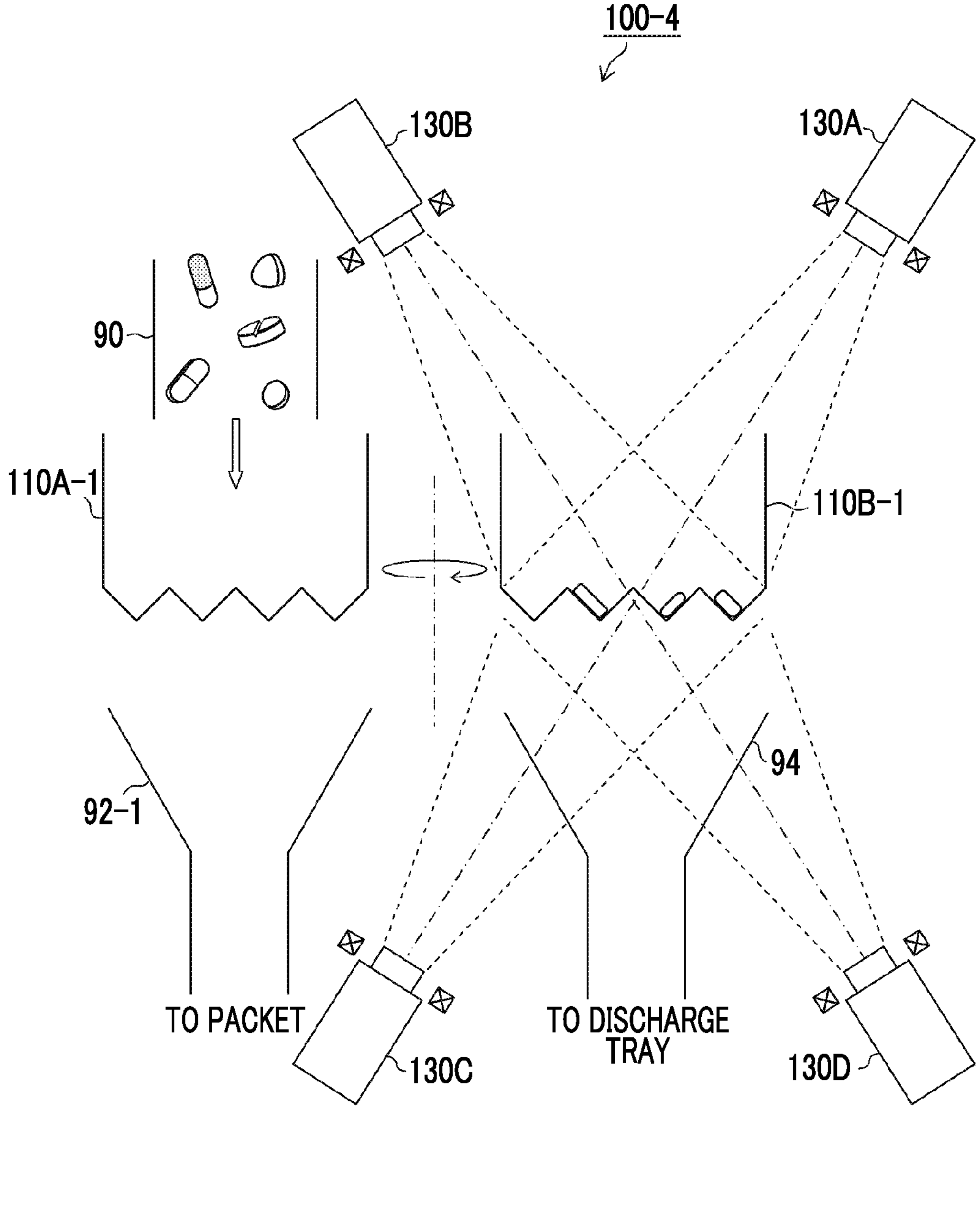

FIG. 19 is a diagram schematically illustrating a main portion of a fourth embodiment of the drug information acquisition device according to the invention.

Figure 20:
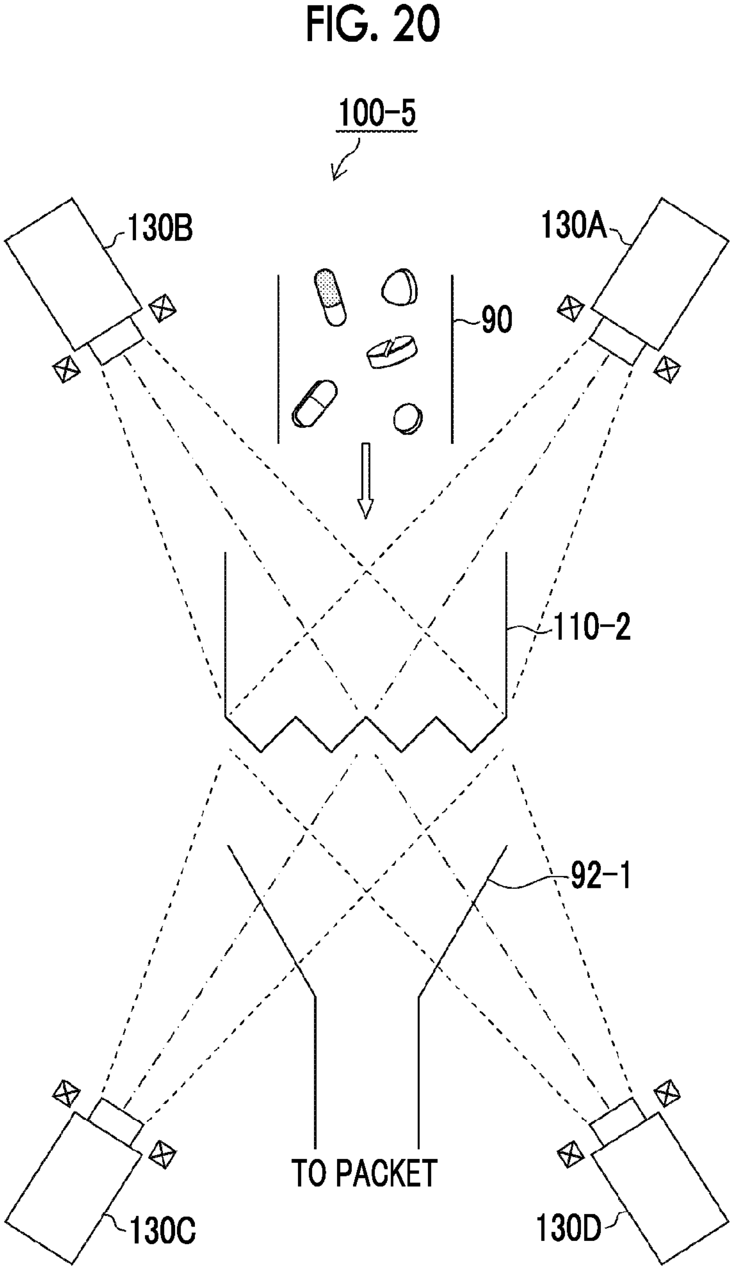

FIG. 20 is a diagram schematically illustrating a main portion of a fifth embodiment of the drug information acquisition device according to the invention.

DESCRIPTION OF THE PREFERRED EMBODIMENTS

Hereinafter, preferred embodiments of a drug information acquisition device and method according to the invention will be described with reference to the accompanying drawings.

[Drug Dispensing inspection Support System]

Figure 1:
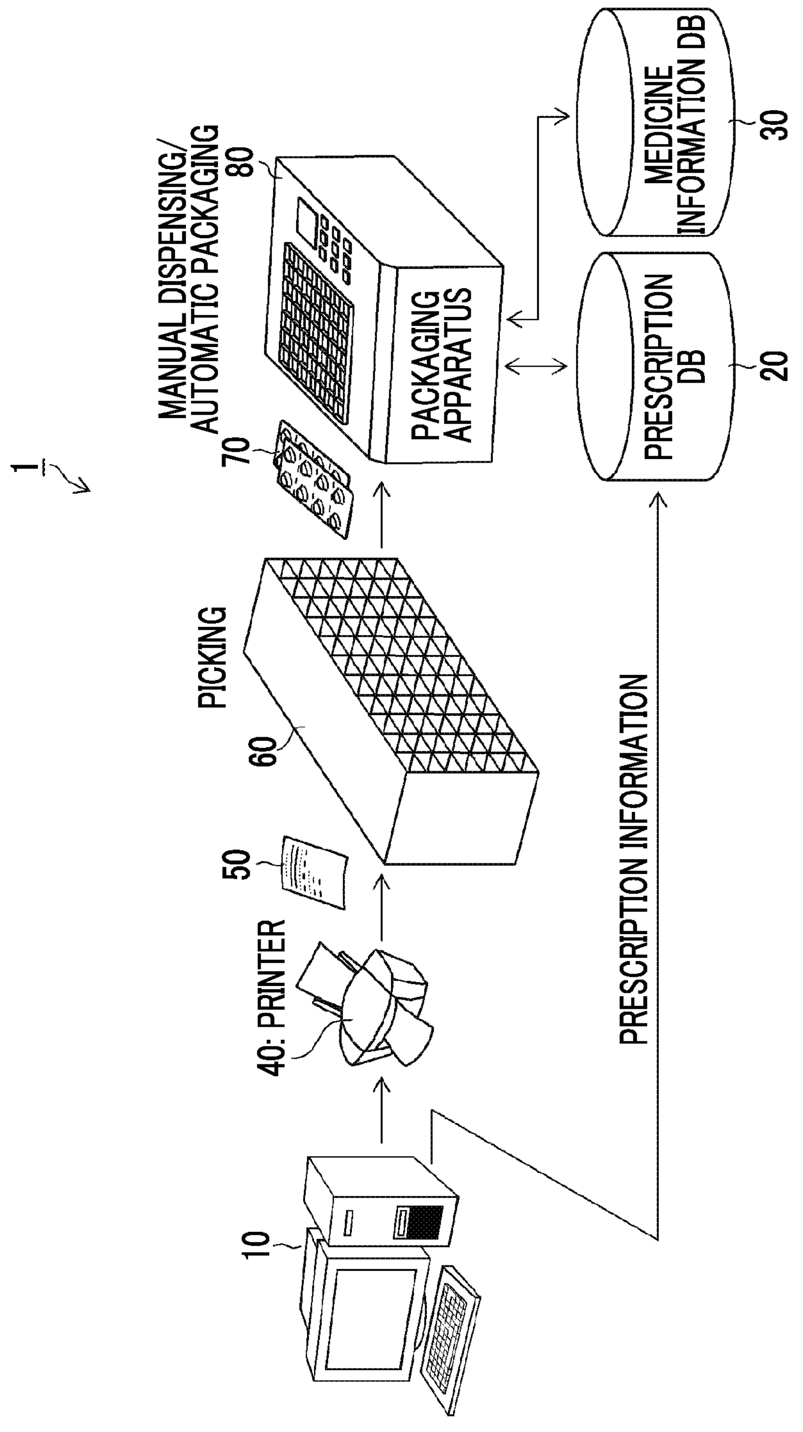
FIG. 1 is a diagram illustrating the overall structure of a drug dispensing inspection support system to which a drug information acquisition device according to the invention is applied.

FIG. 1 is a diagram illustrating the overall structure of a drug dispensing inspection support system to which the drug information acquisition device according to the invention is applied.

A drug dispensing inspection support system 1 illustrated in FIG. 1 mainly includes a terminal 10, such as a personal computer to which prescription information is input, a prescription database (prescription DB) 20 which manages the prescription information, a drug information database (drug information DB) 30 which manages drug information, and a packaging apparatus 80.

Information (prescription information) about a prescription for each patient is input to the terminal 10. The prescription information is transmitted to the prescription DB 20 and is managed. In addition, the prescription information is printed out by a printer 40. There, the prescription information includes, for example, information, such as the type of each dose (morning, noon, and night) of drug which is taken by a patient, the number of days for which the patient takes drug, and the number of doses of drug, associated with prescription identification information (prescription ID), a patient ID, and a prescription date and time.

A pharmacist takes a press-through package (PTP) sheet 70, in which drugs corresponding to a prescription are packaged in a PTP manner, out of a drug shelf 60 while viewing a prescription 50 which is printed out from the printer 40.

Figure 2:
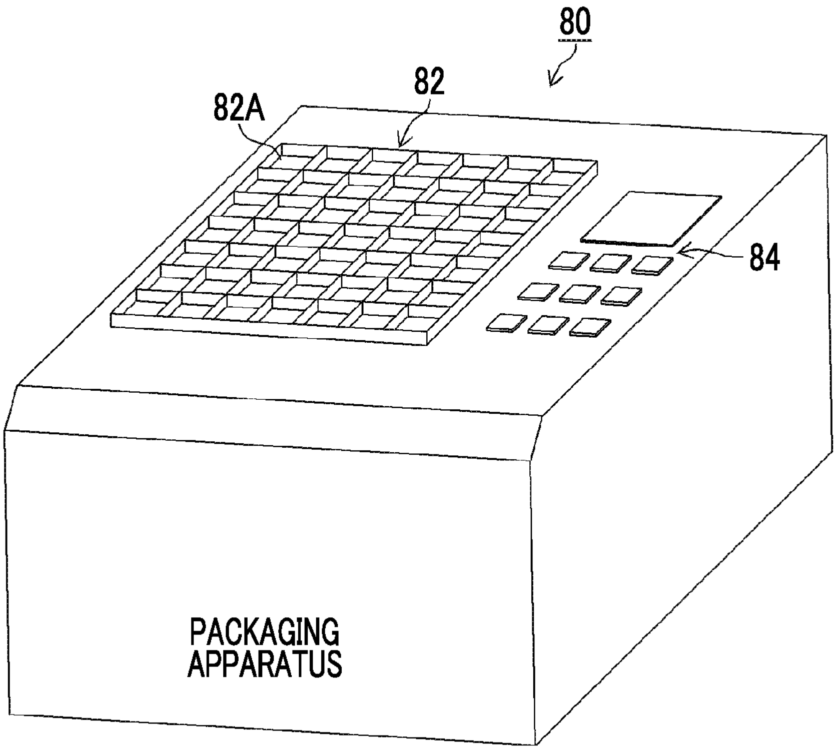
FIG. 2 is a diagram illustrating the outward appearance of a packaging apparatus.

The packaging apparatus 80 inserts a dose of drug which the patent takes at one time into a packet to package each dose of drug and has, for example, a manual distribution tray (drug supply unit) 82 and an operation unit 84 on the upper surface thereof, as illustrated in FIG. 2.

The manual distribution tray 82 has a plurality of containers (cells) 82A which are partitioned in a grid. The pharmacist extracts drugs from the PTP sheet 70 and puts the extracted drugs in each cell 82A of the manual distribution tray 82. The cells 82A are divided so as to correspond to morning, noon, and night and different types of drugs may be put into the cells 82A for morning, noon, and night, according to the prescription. In this way, a so-called manual distribution operation in which a dose of drug is manually put in each cell 82A of the manual distribution tray 82 is performed.

The cells 82A of the manual distribution tray 82 are configured such that the bottoms thereof are individually opened and closed. When the packaging apparatus 80 is operated after the manual distribution operation ends, the packaging apparatus 80 inserts a dose of drug into a packet from each cell 82A of the manual distribution tray 82 through a packet insertion guide. In this way, the packaging apparatus 80 packages drugs.

The drug information acquisition device according to the invention is provided in the packaging apparatus 80 and acquires drug information including outward appearance information of a dose of drug before packaging. In addition, the drug information acquisition device can communicate with the prescription DB 20 and the drug information DB 30 and acquire necessary information from the prescription DB 20 and the drug information DB 30, which will be described below.

[Drug Information Acquisition Device]

<First Embodiment>

Figure 4:
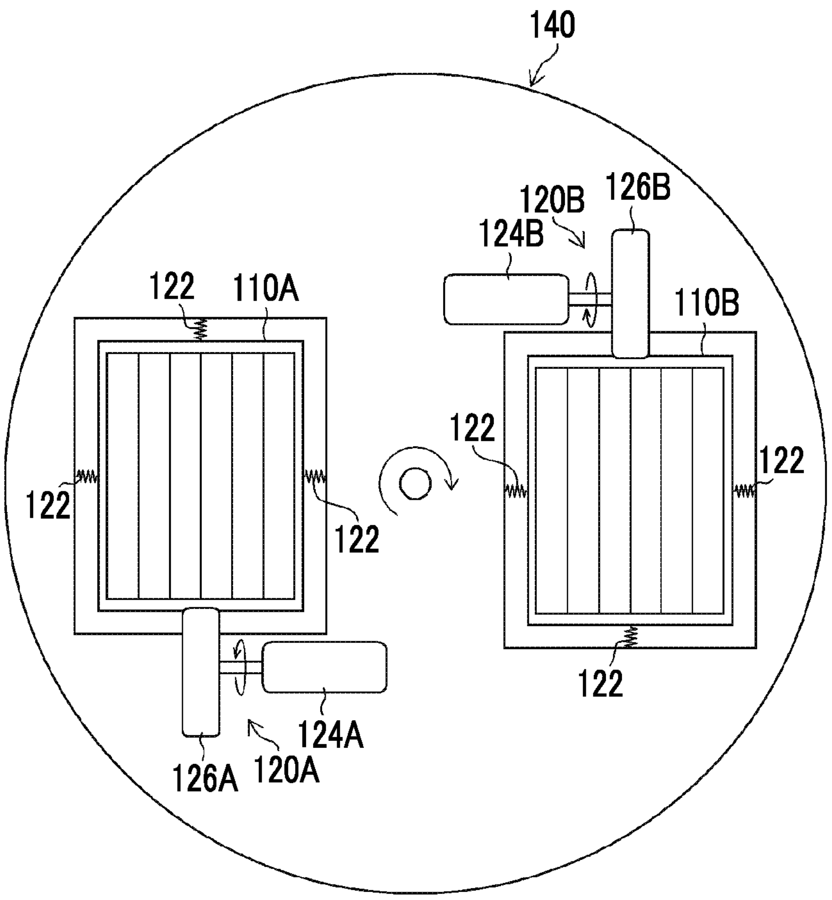
FIG. 4 is a plan view illustrating a main portion of the drug information acquisition device illustrated in FIG. 3.

FIG. 3 is a diagram schematically illustrating a main portion of a first embodiment of the drug information acquisition device according to the invention. FIG. 4 is a plan view illustrating a main portion of the drug information acquisition device illustrated in FIG. 3.

As illustrated in FIG. 3 and FIG. 4, a drug information acquisition device 100-1 mainly includes two imaging trays 110A and 110B which temporarily hold drugs, vibration units (mechanical units) 120A and 120B which vibrate the imaging trays 110A and 110B, two cameras (a first imaging unit and a second imaging unit) 130A and 130B, and a turret device 140 which moves the imaging trays 110A and 110B.

The turret device 140 which holds the imaging trays 110A and 110B is provided between a supply guide (drug supply unit) 90 which guides drugs supplied from each cell 82A of the manual distribution tray 82 and a packet insertion guide 92 and is rotated 180° to switch the positions of the two imaging trays 110A and 110B.

The two imaging trays 110A and 110B have the same shape. When the imaging trays 110A and 110B do not need to be distinguished from each other, they are simply referred to as imaging trays 110.

Figure 5:
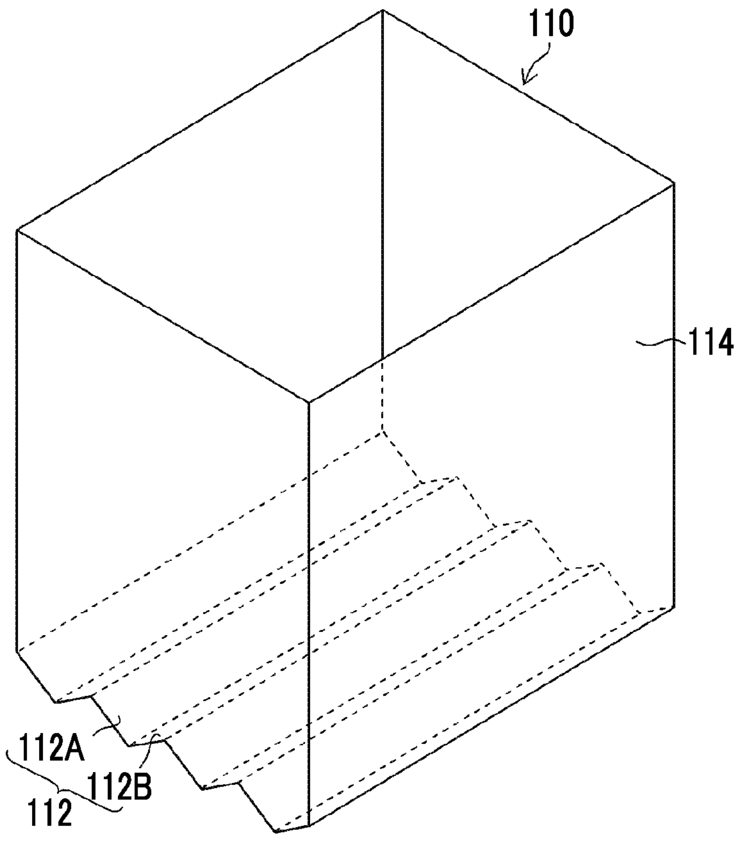
FIG. 5 is a perspective view illustrating an imaging tray illustrated in FIG. 3.

As illustrated in FIG. 5, the imaging tray 110 has a rectangular parallelepiped box shape with an open upper surface and a bottom in which a row of V-shaped grooves 112, each having a first inclined surface 112A and a second inclined surface 112B, is formed. In addition, a side surface 114 of the imaging tray 110 is made of a substantially transparent material.

As illustrated in (a) of FIG. 6, in the V-shaped groove 112 in the bottom of the imaging tray 110, the inclination angle of the first inclined surface 112A and the inclination angle of the second inclined surface 112B with respect to the horizontal plane are equal to each other. In addition, the angle formed between the first inclined surface 112A and the second inclined surface 112B (the angle of the V-shaped groove 112) is preferably equal to or greater than 60 degrees and equal to or less than 150 degrees and more preferably close to 90 degrees. The reason for this is that, when the angle of the V-shaped groove 112 is 90 degrees, the effect of adjusting the posture of the drug is improved.

As illustrated in FIG. 3, the two cameras 130A and 130B are provided so as to face the first inclined surface 112A and the second inclined surface 112B in the bottom of the imaging tray 110, respectively. It is preferable that the angle formed between the optical axes La and Lb of the cameras 130A and 130B is slightly less than the angle of the V-shaped groove 112. In this case, it is possible to prevent some of the drugs from being located in blind slots due to the first inclined surface 112A or the second inclined surface 112B of the V-shaped groove 112.

An imaging tray 110-1 illustrated in (b) of FIG. 6 is a modification example of the imaging tray 110. In a V-shaped groove 112-1 in the bottom of the imaging tray 110-1 according to the modification example, the inclination angle of a first inclined surface 112-1A is different from the inclination angle of a second inclined surface 112-1B. In addition, the angle formed between the first inclined surface 112-1A and the second inclined surface 112-1B is preferably equal to or greater than 60 degrees and equal to or less than 150 degrees and more preferably close to 90 degrees.

As illustrated in FIG. 4, the turret device 140 functions as an imaging tray moving mechanism which holds two imaging trays 110A and 110B and is rotated 180° to switch the positions of the two imaging trays 110A and 110B.

The turret device 140 is provided with the vibration units 120A and 120B which vibrate the imaging trays 110A and 110B, respectively. Each of the imaging trays 110A and 110B is held by the turret device 140 so as to be movable in the horizontal plane and is held at a fixed position in the horizontal plane by four springs 122 (three springs 122 are illustrated in FIG. 4).

The vibration unit 120A includes an electric motor 124A and an eccentric cam 1264 and a cam surface of the eccentric cam 126A comes into contact with the side surface of the imaging tray 110A. Similarly, the vibration unit 120B includes an electric motor 124B and an eccentric cam 126B and a cam surface of the eccentric cam 1263 comes into contact with the side surface of the imaging tray 110B. Therefore, the electric motors 124A and 124B rotate the eccentric cams 126A and 126B to vibrate the imaging trays 110A and 110B in the horizontal plane, respectively.

In this embodiment, the vibration units 120A and 120B illustrated in FIG. 4 vibrate the imaging trays 110A and 110B in the direction of the V-shaped groove 112 in the bottom of the imaging trays 110A and 110B, respectively. However, the invention is not limited thereto. For example, the vibration units 120A and 120B may vibrate the imaging trays 110A and 110B in an oblique direction with respect to the groove direction of the V-shaped groove 112, or in two directions, that is, the groove direction and a direction perpendicular to the groove direction. The structure of the vibration unit is not limited to this embodiment and the vibration unit may have any structure as long as it can vibrate the imaging tray 110.

Returning to FIG. 3, the drug information acquisition device 100-1 has two positions, that is, an insertion position (supply position) where the drugs from the supply guide 90 are inserted (supplied) into the imaging tray 110 and a position (imaging position) where the image of the drugs in the imaging trays 110 is captured. The turret device 140 (FIG. 4) is rotated 180° to switch the two imaging trays 110A and 110B between the insertion position and the imaging position.

In the first embodiment, the insertion position where drugs are inserted is also a position where the vibration units 120A or 120B vibrate the imaging trays 110. In addition, the imaging position is also a discharge position where the drugs in the imaging trays 110 are discharged to the packet insertion guide 92.

As illustrated in FIG. 3, the two cameras 130A and 130B capture the images of the drugs in the imaging trays 110 moved to the imaging position in different directions and are provided in an obliquely upward direction with respect to the imaging tray 110. That is, the camera 130A is provided so as to face the first inclined surface 112A in the bottom of the imaging tray 110 and the camera 130B is provided so as to face the second inclined surface 112B in the bottom of the imaging tray 110.

In addition, ring illumination units 150A and 150B (illumination units) are provided around lens units of the two cameras 130A and 130B, respectively. The ring illumination units 150A and 150B uniformly illuminate the entire bottom of the imaging tray 110 such that no shadows occur due to the drugs.

Before the two cameras 130A and 130B capture the images of the drugs, the vibration unit 120A or 120B vibrates the imaging tray 110 having a dose of drug inserted thereinto.

(a) of FIG. 7 illustrates the state of the drugs in the imaging tray 110 immediately after the drugs are inserted and (b) of FIG. 7 illustrates the state of the drugs in the imaging tray 110 after the imaging tray 110 is vibrated.

As illustrated in (a) of FIG. 7, some of the inserted drugs overlap each other in the imaging tray 110 or the posture of some of the drugs is irregular. However, when the imaging tray 110 is vibrated, the overlap between the drugs can be removed and the posture of the drugs can be corrected (adjusted) by the first inclined surface 112A and the second inclined surface 112B of the V-shaped groove 112, as illustrated in (b) of FIG. 7.

For example, the posture of a disc-shaped drug is adjusted such that the upper surface or the lower surface of the drug is located along the first inclined surface 112A or the second inclined surface 112B of the V-shaped groove 112. The posture of a capsule-shaped drug or a straw-bale-shaped drug is adjusted such that the longitudinal direction of the drug is aligned with the direction of the V-shaped groove 112.

Therefore, after the imaging tray 110 is vibrated, as illustrated in FIG. 3, the two cameras 130A and 130B capture the images of the drugs in the imaging tray 110 in two directions to capture the images of the upper (or lower) and side surfaces of the drugs. However, in the case of the capsule-shaped drug, the images of different side surfaces of the drug are captured.

The images (a first image and a second image) captured by the two cameras 130A and 130B are processed by a drug information acquisition unit 170 (FIG. 9), which will be described below. In this way, it is possible to acquire drug information including at least the outward appearance information of the drug. The acquired drug information can be used to determine whether a dose of drug is dispensed according to the prescription.

When the capture of the images of the drugs by the two cameras 130A and 130B ends, the drugs are discharged from the imaging tray 110 to the packet insertion guide 92.

As illustrated in FIG. 8, the bottom of the imaging tray 110 at the imaging position can be opened by a drug discharge unit 190 (FIG. 9) to discharge the drugs from the imaging tray 110 to the packet insertion guide 92. The discharge of the drugs from the imaging tray 110 to the packet insertion guide 92 is not limited to the method which opens the bottom of the imaging tray 110. For example, the following various methods can be applied: a method which opens the side surface of the imaging tray and inclines the imaging tray to drop drugs or to sweep the drugs out of the imaging tray; and a method which upturns the imaging tray.

<Internal Structure of Drug Information Acquisition Device>

FIG. 9 is a block diagram illustrating an embodiment of the internal structure of the drug information acquisition device 100-1.

As illustrated in FIG. 9, the drug information acquisition device 100-1 includes, for example, the operation unit 84, a control unit 160, a drug information acquisition unit 170, a determination result output unit 180, and the drug discharge unit 190 in addition to the imaging tray 110, the vibration unit 120A (120B), the cameras 130A and 130B, the turret device 140, and the ring illumination units 150A and 150B.

The control unit 160 controls the overall operation of each unit of the drug information acquisition device 100-1. In addition, the control unit 160 can communicate with the prescription DB 20 and the drug information DB 30 to acquire necessary information from the prescription DB 20 and the drug information DB 30 and can communicate with the packaging apparatus 80 (FIG. 2) to control synchronization with a packaging operation.

The operation unit 84 is provided on an operation surface of the packaging apparatus 80 (FIG. 2) and receives, for example, a prescription ID described in the prescription 50 (FIG. 1) and the operation information of the packaging apparatus 80.

When the prescription ID is input from the operation unit 84, the control unit 160 reads prescription information (for example, the type of a dose of drug which is taken by the patient, the number of days for which the patent takes the drug, and the number of drugs corresponding to a dose) corresponding to the input prescription ID from the prescription information managed by the prescription DB 20. In addition, the control unit 160 reads drug information corresponding to each type of drug from the drug information DB 30, on the basis of the read prescription information. The control unit 160 outputs the read prescription information and drug information as reference information of a dose of drug to the drug information acquisition unit 170.

Here, the drug information corresponding to the type of drug is information about the form of the drug (for example, an outward appearance, a color, a character, and a secant line). The outward appearance information of the drug is information including the shape of drug (for example, a disc shape, a lens shape, a capsule shape, a straw bale shape, a triangular shape, and a football shape) and a size (for example, a diameter, a thickness, a major axis, and a minor axis). The color information of the drug is information indicating the color of the drug under a standard light source (under the same illumination as the ring illumination). For example, the proportions of red (R), green (G), and blue (B) and color difference information are considered as the color information. The character information of the drug is information about characters which are printed or stamped on the surface of the drug.

The control unit 160 outputs an imaging instruction and an illumination instruction to the two cameras 130A and 130B and the ring illumination units 150A and 150B at a predetermined time, respectively.

The drug information acquisition unit 170 processes two images captured by the two cameras 130A and 130B to acquire drug information related to the shape of each drug in a packet.

As illustrated in FIG. 3, since the two cameras 130A and 130B are provided so as to face the first inclined surface 112A and the second inclined surface 112B in the bottom of the imaging tray 110, respectively, the two images captured by the cameras 130A and 130B include the image of the upper surface (or the lower surface) of the drug and the image of the side surface of the drug.

For example, as illustrated in (a) and (b) of FIG. 10, the side surface of a disc-shaped drug 200 and the side surface of a lens-shaped drug 202 have different shapes. Therefore, the drug information acquisition unit 170 can distinguish the disc-shaped drug 200 and the lens-shaped drug 202 even though the drugs 200 and 202 have the same diameter. In addition, when disc-shaped drugs have the same diameter, but have different thickness, the drugs can be determined to be different types of drugs.

In addition, (a) and (b) of FIG. 11 are diagrams illustrating an example of two images which are captured in a direction perpendicular to the first inclined surface 112A of the V-shaped groove 112 in the bottom of the imaging tray 110 and a direction perpendicular to the second inclined surface 112B of the V-shaped groove 112.

The captured image illustrated in (a) of FIG. 11 includes the image of the upper surface (or the lower surface) of the drug 210 and the image of the side surface of the drug 212, of two types of disc-shaped drugs 210 and 212 with different diameters. The captured image illustrated in (b) of FIG. 11 includes the image of the side surface of the drug 210 and the image of the upper surface (or the lower surface) of the drug 212.

As illustrated in FIG. 11, even though the drugs 210 and 212, whose posture has been adjusted along the first inclined surface 112A and the second inclined surface 112B of the V-shaped groove 112, do not overlap each other, they seem to largely overlap each other on the image illustrated in (b) of FIG. 11 due to, for example, the shapes of adjacent drugs.

Even when the images of the drugs overlap each other in one captured image, the drug information acquisition unit 170 can perform image processing for two captured images to accurately calculate the outward appearance information of the drugs from the relationship with the images of the drugs which appear in the other image captured in a different direction.

The drug information acquisition unit 170 includes a storage unit 170B that stores size correction information corresponding to the object distance of each V-shaped groove 112 in the row of the grooves in the bottom of the imaging tray 110.

As illustrated in FIG. 3, the camera 130A captures the image of the drug in a direction that is substantially perpendicular to the first inclined surface 112A of the V-shaped groove 112. However, the object distance to the first inclined surface 112A of the V-shaped groove 112 varies depending on the position of the V-shaped groove 112. As a result, the size of the same drug in the captured image varies depending on which of the V-shaped grooves 112 in the row of the grooves the drug is located in.

The storage unit 170B stores the size correction information corresponding to the position (that is, the object distance) of the V-shaped groove 112. The drug information acquisition unit 170 reads the size correction information of the captured drug corresponding to the position of the V-shaped groove 112 from the storage unit 170B and corrects the size information of the drug obtained by image processing, on the basis of the read size correction information. Therefore, whichever V-shaped groove 12 in the row of the grooves in the bottom of the imaging tray 110 the drug is located in, it is possible to accurately acquire the size of the drug. For example, it is possible to detect the size of the drug in an error range of about 0.1 mm.

The drug information acquisition unit 170 acquires color information indicating the color of the drug as the drug information on the basis of the captured image. Therefore, even when drugs 220 and 222 have the same shape as illustrated in (a) and (b) of FIG. 12, the drugs 220 and 222 with different color information items can be determined to be different types of drugs. The color information includes information of different colors illustrated in (a) of FIG. 12.

The drug information acquisition unit 170 acquires the character information of the drug and a secant line as the drug information on the basis of the captured image.

(a) of FIG. 13 illustrates a drug 230 having characters printed or stamped on the surface thereof and (b) of FIG. 13 illustrates a drug 232 having a secant line 232 formed therein.

The drug information acquisition unit 170 has an optical character recognition (OCR) function and reads the characters which are printed or stamped on the surface of the drug in the captured image. When a drug has a secant line, the drug information acquisition unit 170 detects the secant line. Therefore, even if drugs have the same shape and color, the drug information acquisition unit 170 can recognize different types of drugs on the basis of the character information or the secant line.

The drug information acquisition unit 170 compares the acquired drug information of a dose of drug with the drug information reference information) of a dose of drug which is input from the control unit 160 and then extracted on the basis of the prescription information. When the drug information of all of the drugs corresponding to a dose is identical to the reference information, the drug information acquisition unit 170 determines that a dose of drug is dispensed according to the prescription. When the drug information of any of the drugs corresponding to a dose is not identical to the reference information and when the number of drugs is not equal to that in the reference information, the drug information acquisition unit 170 determines that a dose of drug is not dispensed according to the prescription and outputs the determination result to the determination result output unit 180.

The determination result output unit 180 records or displays the determination results. For example, the determination result output unit 180 can record or display information indicating the day at which the doses of drug for morning and noon are different from those in the prescription. Therefore, even when drugs are exchanged between adjacent cells 82A of the manual distribution tray 82 during the manual distribution operation using the manual distribution tray 82 illustrated in FIG. 2 (that is, even when the number of drugs corresponding to a dose is correct), it is possible to obtain the determination result indicating whether a dose of drug is different from that in the prescription.

The control unit 160 operates the vibration unit 120A (120B), the turret device 140, and the drug discharge unit 190 at an appropriate time in synchronization with the packaging operation of the packaging apparatus 80.

<Drug Information Acquisition Method>

Next, an embodiment of the drug information acquisition method according to the invention will be described.

FIG. 14 is a flowchart illustrating the procedure of the process of the drug information acquisition device 100-1 according to the first embodiment.

It is assumed that the manual distribution operation of the pharmacist for the manual distribution tray 82 and the input of the prescription ID by the operation unit 84 end prior to the acquisition of the drug information by the drug information acquisition device 100-1.

In FIG. 14, when the packaging apparatus 80 starts automatic packaging, a dose of drug accommodated in the cell 82A of the manual distribution tray 82 is inserted into the imaging tray 110 at a drug insertion/vibration position through the supply guide 90, as illustrated in FIG. 3 (Step S10; a drug supply step). The drug insertion operation may be performed by the function of the packaging apparatus 80.

Then, the vibration unit 120A or 120B vibrates the imaging tray 110 which is located at the drug insertion/vibration position and into which a dose of drug is inserted for a predetermined period of time (Step S12; a vibration step). The vibration time is a sufficient time to remove the overlap between the drugs corresponding to a dose supplied to the imaging tray 110 and to adjust the posture of the drugs using the first inclined surface 112A and the second inclined surface 112B of the V-shaped groove 112 in the bottom of the imaging tray 110.

Then, the positions of the two imaging trays 110A and 110B are exchanged by the turret device 140 (the imaging tray is moved) (Step S14). Then, the imaging tray 110 at the drug insertion/vibration position is moved to the imaging/drug discharge position.

Then, the image of a dose of drug in the imaging tray 110 moved to the imaging/drug discharge position is captured by the two cameras 130A and 130B and two captured images are acquired (Step S16; an imaging step). The drug information acquisition unit 170 processes each of the two captured images to acquire the drug information including at least the outward appearance information of the drug (drug information acquisition step), as described above.

When the imaging of the drug ends, the drug is discharged from the imaging tray 110 to the packet insertion guide 92 (Step S18). The packaging apparatus 80 inserts a dose of drug discharged to the packet insertion guide 92 into a packet and packages the drug.

Then, the drug information acquisition device 100-1 or the packaging apparatus 80 determines whether an operation of packaging drugs corresponding to one patient has ended (Step S20). When the operation has not ended ("No"), the drug information acquisition device 100-1 or the packaging apparatus 80 proceeds to Step S10 and repeats the process from Step S10 to Step S18. When the operation has ended ("Yes"), the drug information acquisition device 100-1 or the packaging apparatus 80 ends the packaging process.

The process in Step S10 and Step S12 is the process at the drug insertion/vibration position and the process in Step S14 and Step S16 is the process at the imaging/drug discharge position. Therefore, these processes can be performed in parallel.

FIG. 15 is a timing chart illustrating the procedure of the process of the drug information acquisition device 100-1 at the drug insertion/vibration position and the imaging/drug discharge position.

As illustrated in FIG. 15, it is possible to perform the process at the drug insertion/vibration position ((a) of FIG. 15) and the process at the imaging/drug discharge position ((c) of FIG. 15) at the same time (in parallel) except for a period ((b) of FIG. 15) for exchanging the positions of the two imaging trays 110A and 110B (moving the imaging trays).

In this way, it is possible to continuously perform the drug insertion process, the vibration process, the imaging tray moving process, the imaging process, and the drug discharge process in this order with a period T. In particular, when the period T is within the period of time required for the packaging apparatus to package a dose of drug, it is possible to prevent a reduction in the packaging speed of the packaging apparatus. When the processes are performed in parallel, it is possible to prevent a significant reduction in the packaging speed even if the period T is beyond the period of time required for the packaging apparatus to package a dose of drug. In addition, it is possible to vibrate the imaging tray for a period from the insertion of the drug to the imaging of the drug and thus to shorten the period T.

<Modification Example of First Embodiment>

A drug information acquisition device according to a modification example of the first embodiment further includes an image acquisition unit (the control unit 160 and the drug information acquisition unit 170 illustrated in FIG. 9) which instructs the cameras 130A and 130B to continuously capture the image of drugs on the imaging tray 110 which is being vibrated to acquire continuous images, a determination unit (the drug information acquisition unit 170) which processes each of the images acquired by the image acquisition unit to remove the overlap between the drugs corresponding to a dose supplied to the imaging tray 110 and to determine whether the posture of the drugs has been corrected, and a control unit 160 that stops the vibration of the imaging tray 110 by the vibration unit 120A or 120B when the determination unit determines that the overlap between the drugs has been removed and the posture of the drugs has been corrected.

FIG. 16 is a flowchart illustrating the procedure of the process of the drug information acquisition device according to the modification example of the first embodiment. The same portions as those in the flowchart including the procedure of the process of the drug information acquisition device 100-1 according to the first embodiment illustrated in FIG. 14 are denoted by the same step numbers and the description thereof will not be repeated.

In FIG. 16, immediately after the insertion of drugs into the imaging tray 110 at the drug insertion/vibration position in Step S10 ends, the vibration of the imaging tray 110 by the vibration unit 120A or 120B immediately starts (Step S30; a vibration step).

Then, when the imaging tray 110 is moved to the imaging/drug discharge position, the cameras 130A and 130B continuously capture the image of the drugs on the imaging tray 110 which is being vibrated (first imaging step) and image processing for removing the overlap between the drugs corresponding to a dose supplied to the imaging tray 110 on the basis of the continuously captured images and for determining whether the posture of the drugs has been corrected is performed (Step S32).

Here, the image processing is required to remove the overlap between the drugs and to correct the posture of the drugs. Therefore, a predetermined shape range is determined from the "shape of the drugs to be present" which has been acquired in advance from the prescription DB 20 and the drug information DB 30 and image processing is performed to compare the shape of each drug which can be obtained in a state in which the drugs in the imaging tray 110 do not overlap each other with the shape of each drug in the captured image. In addition, as another image processing, the following image processing is considered: image processing for determining whether each of the drugs in the imaging tray 110 has the same posture in two successive images (that is, whether the posture of each drug is adjusted and stabilized by the V-shaped grooves 112 in the bottom of the imaging tray 110).

The resolution of the image which is captured during vibration is reduced by the influence of image blurring. However, since the image is used for image processing for determining the overlap between the drugs, the quality of the image is sufficient to determine the overlap between the drugs.

Then, it is determined whether, for example, the overlap between the drugs corresponding to a dose in the imaging tray 110 has been removed on the basis of the image processing in Step S32 (Step S34; a determination step). When it is determined that the overlap between the drugs has not been removed ("No"), the process proceeds to Step S32. Then, the next image is captured and image processing is performed for the captured image. When it is determined that the overlap between the drugs has been removed ("Yes"), the process proceeds to Step S36.

In Step S36, the control unit 160 issues a vibration stop instruction to the vibration unit 120A or 120B to stop the vibration of the imaging tray 110 (vibration stop step).

When the vibration of the imaging tray 110 is stopped, the cameras 130A and 130B capture the image of a dose of drug in the imaging tray 110 in a stationary state (Step S38; a second imaging step) Step S38 corresponds to Step S16 illustrated in FIG. 14 and the drug information acquisition unit 170 performs image processing for each of two captured images to acquire drug information including at least the outward appearance information of the drug.

As such, according to the modification example of the first embodiment, the image of a dose of drug in the imaging tray 110 which is being vibrated is continuously captured and the vibration of the imaging tray 110 is stopped at the time when it is determined that the overlap between the drugs has been removed on the basis of the continuously captured images. Therefore, it is possible to shorten the vibration time.

Only one of the cameras 130A and 130B may continuously capture the image of the drug in the imaging tray 110 while the imaging tray 110 is being vibrated. In this case, it is possible to determine whether, for example, the overlap between the drugs has been removed on the basis of the time-series image captured by one of the cameras.

<Second Embodiment>

FIG. 17 is a diagram schematically illustrating a main portion of a second embodiment of the drug information acquisition device according to the invention. The same components as those in the drug information acquisition device 100-1 according to the first embodiment illustrated in FIG. 3 are denoted by the same reference numerals and the detailed description thereof will not be repeated.

A drug information acquisition device 100-2 according to the second embodiment illustrated in FIG. 17 differs from the drug information acquisition device 100-1 according to the first embodiment in the structure of two imaging trays 110A-1 and 110B-1 and the arrangement position of two cameras 130C and 130D and a packet insertion guide 92-1.

That is, the bottom of each of the two imaging trays 110A-1 and 110B-1 is a transparent member and the cameras 130C and 130D are provided in an obliquely downward direction with respect to the imaging tray 110B-1 and capture the image of drugs through the transparent member at the bottom. The packet insertion guide 92-1 is provided so as to be opposite to the supply guide 90 and does not fall within an imaging region of the cameras 130C and 130D.

In the drug information acquisition device 100-2 according to the second embodiment, the cameras 130C and 130D are provided below the imaging tray 110B-1. Therefore, the drug information acquisition device 100-2 is useful for a case in which a camera installation space (a space capable of ensuring an object distance) is below the supply guide 90.

<Third Embodiment>

FIG. 18 is a diagram schematically illustrating a main portion of a third embodiment of the drug information acquisition device according to the invention. The same components as those in the drug information acquisition device 100-1 according to the first embodiment illustrated in FIG. 3 and the drug information acquisition device 100-2 according to the second embodiment illustrated in FIG. 17 are denoted by the same reference numerals and the detailed description thereof will not be repeated.

A drug information acquisition device 100-3 according to the third embodiment illustrated in FIG. 18 is a combination of the drug information acquisition device 100-1 according to the first embodiment and the drug information acquisition device 100-2 according to the second embodiment and particularly includes cameras 130A and 130B (a first imaging unit and a second imaging unit) and cameras 130C and 130D (a third imaging unit and a fourth imaging unit).

The camera 130A and the camera 130C are provided so as to face each other, with the bottom of the imaging tray 110B-1, which is a transparent member, interposed therebetween. Similarly, the camera 130B and camera 130D are provided so as to face each other, with the bottom of the imaging tray 110B-1, which is the transparent member, interposed therebetween.

Since four cameras 130A 130B, 130C, and 130D are arranged in this way, it is possible to acquire four captured images (first to fourth images). The images of the upper, lower, and two opposite side surfaces of one drug are obtained.

According to this structure, when character information is printed or stamped on the surface of a drug or when a secant line is engraved in the drug as shown in FIG. 13, it is possible to reliably capture the image of the character information or the secant line.

<Fourth Embodiment>

FIG. 19 is a diagram schematically illustrating a main portion of a fourth embodiment of the drug information acquisition device according to the invention. The same components as those in the drug information acquisition device 100-3 according to the third embodiment illustrated in FIG. 18 are denoted by the same reference numerals and the detailed description thereof will not be repeated.

A drug information acquisition device 100-4 according to the fourth embodiment illustrated in FIG. 19 mainly differs from the drug information acquisition device 100-3 according to the third embodiment in that it further includes a discharge guide 94.

The discharge guide 94 is a guide portion which discharges a dose of drug, which has been determined not to be dispensed according to a prescription, to a discharge tray (not illustrated). At least a portion of the discharge guide 94 is a transparent member such that the discharge guide 94 does not hinder the cameras 130C and 130D from capturing images.

When it is determined that a dose of drug has not been dispensed according to a prescription, a drug information acquisition unit of the drug information acquisition device 100-4 outputs the determination result to the determination result output unit 180. In addition, since the discharge guide 94 is provided, the drug information acquisition unit discharges the dose of drug, which has been determined not to be dispensed according to the prescription, to the discharge tray through the discharge guide 94. Therefore, it is possible to prevent the packaging apparatus 80 from packaging the dose of drug which has been determined not to be dispensed according to the prescription.

In the drug information acquisition device 100-4 according to the fourth embodiment, the arrangement position of the packet insertion guide 92-1 and the arrangement position of the discharge guide 94 may be exchanged.

<Fifth Embodiment>

FIG. 20 is a diagram schematically illustrating a main portion of a fifth embodiment of the drug information acquisition device according to the invention. The same components as those in the drug information acquisition device 100-3 according to the third embodiment illustrated in FIG. 18 are denoted by the same reference numerals and the detailed description thereof will not be repeated.

A drug information acquisition device 100-5 according to the fifth embodiment illustrated in FIG. 20 mainly differs from the drug information acquisition device 100-3 according to the third embodiment in that it includes only a single imaging tray 110-2 and the imaging tray 110-2 is not moved.

The bottom and side of the imaging tray 110-2 and a portion of the packet insertion guide 92-1 are transparent members such that the cameras 130A, 130B, 130C, and 130D are not hindered from capturing the images of drugs.

According to the drug information acquisition device 100-5 of the fifth embodiment, it is possible to omit a moving mechanism such as a turret device for moving the imaging tray to the imaging position. Therefore, it is possible to reduce the size and cost of the device.

The drug information acquisition device 100-5 according to the fifth embodiment includes four cameras 130A, 130B, 130C, and 130D. However, only two cameras 130A and 130B which capture the image of the bottom of the imaging tray 110-2 from the upper side or only two cameras 130C and 130D which capture the image of the bottom of the imaging tray 110-2 from the lower side may be provided.

<Others>

As illustrated in FIG. 5, the imaging tray 110 according to this embodiment has the rectangular parallelepiped box shape with the open upper surface. However, the invention is not limited thereto. The imaging tray 110 may be inclined such that the side surface of the imaging tray does not fall within the imaging range when the cameras 130A and 130B capture images.

The drug supply unit according to this embodiment includes the manual distribution tray 82 and a dose of drug is inserted from the manual distribution tray 82 to the imaging tray 110 through the supply guide 90. However, the invention is not limited thereto. The invention may be applied to an automatic drug supply device which automatically supplies a dose of drug.

In addition, in the above-described embodiments, the vibration unit vibrates the imaging tray to prevent the overlap between the drugs corresponding to a dose which are inserted into the imaging tray and to adjust the posture of the drugs. However, the invention is not limited to the structure in which the imaging tray is vibrated. For example, an operation of sweeping the imaging tray with a brush group may be performed to prevent the overlap between the drugs and to adjust the posture of the drugs.

The invention is not limited to the above-described embodiments and various modifications and changes of the invention can be made without departing from the scope and spirit of the invention.

EXPLANATION OF REFERENCES

1: DRUG DISPENSING INSPECTION SUPPORT SYSTEM
80: PACKAGING APPARATUS
82: MANUAL DISTRIBUTION TRAY
82A: CELL
84: OPERATION UNIT
90: SUPPLY GUIDE
92, 92-1: PACKET INSERTION GUIDE
100-1 TO 100-5: DRUG INFORMATION ACQUISITION DEVICE
110, 110A, 110B, 110-1, 110-2, 110A-1, 110B-1: IMAGING TRAY
112, 112-1: V-SHAPED GROOVE
112A, 112-1A: FIRST INCLINED SURFACE
112B, 112-1B: SECOND INCLINED SURFACE
120A, 120B: VIBRATION UNIT
130A, 130B, 130C, 130D: CAMERA
140: TURRET DEVICE
150A, 150B: RING ILLUMINATION
160: CONTROL UNIT
170: DRUG INFORMATION ACQUISITION UNIT
170B: STORAGE UNIT
200, 202, 210, 212, 220, 222, 230, 232: DRUG
232A: SECANT LINE

What is claimed is:

1. A drug information acquisition device comprising:

an imaging tray that is provided between a drug distribution tray which supplies each dose of a plurality of types of drugs and a packet insertion guide, said imaging tray temporarily holds a dose of drug supplied from the drug distribution tray for imaging, said imaging tray having a bottom in which a row of V-shaped grooves, each having a first inclined surface and a second inclined surface, is formed;

a vibrator that removes an overlap between the drugs corresponding to a dose supplied to the imaging tray and corrects the posture of the drugs using the first inclined surface and the second inclined surface of at least one of the V-shaped grooves;

a light source that illuminates the drugs on the imaging tray;

a first camera and a second camera that are provided so as to face the first inclined surface and the second inclined surface in the bottom of the imaging tray, respectively, and capture images of the drugs, whose posture is corrected by the vibrator and which are illuminated by the light source, on the imaging tray; and a drug information acquisition computer configured to process a first image and a second image which are respectively acquired from the first camera and the second camera to acquire drug information including at least outward appearance information of the drugs in the first image and the second image.

2. The drug information acquisition device according to claim 1, further comprising:

a moving mechanism; and a processor, wherein a plurality of the imaging trays are provided, the moving mechanism moves the plurality of imaging trays between at least two of a position where the drug is supplied from the drug distribution tray to the imaging tray, a position where the vibrator vibrates the imaging tray, a position where the first camera and the second camera capture the image of the drug in the imaging tray, and a position where the drug is discharged from the imaging tray to the packet insertion guide after the image capture, and the processor simultaneously operates the plurality of imaging trays at the two or more positions.

3. The drug information acquisition device according to claim 1, further comprising:

an image acquisition computer configured to instruct at least one of the first camera and the second camera to continuously capture the image of the drug on the imaging tray while the vibrator is vibrating the imaging tray and acquires a continuous image;

a determination computer configured to determine whether the overlap between the drugs corresponding to a dose supplied to the imaging tray has been removed and whether the posture of the drugs has been corrected, on the basis of the image acquired by the image acquisition computer; and a control computer configured to stop the vibration of the imaging tray by the vibrator when the determination computer determines that the overlap between the drugs has been removed and that the posture of the drugs has been corrected, wherein the drug information acquisition computer acquires the drug information on the basis of the first image and the second image which are acquired from the first camera and the second camera, respectively, after the vibration of the imaging tray is stopped.

4. The drug information acquisition device according to claim 1, wherein the first inclined surface and the second inclined surface of the V-shaped groove have the same inclination angle, and an angle formed between the first inclined surface and the second inclined surface is equal to or greater than 60 degrees and equal to or less than 150 degrees.

5. The drug information acquisition device according to claim 1, wherein the first inclined surface and the second inclined surface of the V-shaped groove have different inclination angles, and an angle formed between the first inclined surface and the second inclined surface is equal to or greater than 60 degrees and equal to or less than 150 degrees.

6. The drug information acquisition device according to claim 1, wherein the drug information acquisition computer includes a memory that stores size correction information corresponding to an object distance of each V-shaped groove in the row of the V-shaped grooves in the bottom of the imaging tray, reads the corresponding size correction information from the memory according to which of the V-shaped grooves in the row of the V-shaped grooves of the imaging tray the drug is located in, and corrects size information which is included in the outward appearance information acquired by the image processing with the read size correction information.

7. The drug information acquisition device according to claim 1, wherein the first camera and the second camera are provided in an obliquely upward direction with respect to the imaging tray.

8. The drug information acquisition device according to claim 7, further comprising:

a third camera and a fourth camera that are provided so as to face the first camera and the second camera, respectively, with the imaging tray interposed therebetween, wherein at least the bottom of the imaging tray is a transparent member, the third camera and the fourth camera capture images of the drugs through the transparent member, and the drug information acquisition computer processes each of first to fourth images acquired by the first to fourth cameras to acquire drug information including at least outward appearance information of the drugs in the first to fourth images.

9. The drug information acquisition device according to claim 1, wherein at least the bottom of the imaging tray is a transparent member, and the first camera and the second camera are provided in an obliquely downward direction with respect to the imaging tray and capture the image of the drug through the transparent member.

10. The drug information acquisition device according to claim 1, wherein the drug information acquisition computer is configured to further acquire at least one of color information, character information, and a secant line of the drug in the image, using the image processing.

11. A drug information acquisition method that is performed in a drug information acquisition device including an imaging tray that is provided between a drug distribution tray and a packet insertion guide and has a bottom in which a row of V-shaped grooves, each having a first inclined surface and a second inclined surface, is formed, a vibrator that vibrates the imaging tray, light source that illuminates drugs on the imaging tray, a first camera and a second camera that are provided so as to face the first inclined surface and the second inclined surface in the bottom of the imaging tray, respectively, and a drug information acquisition computer, the method comprising:

a drug supply step of supplying each dose of a plurality of types of drugs from the drug distribution tray to the imaging tray;

a vibration step of vibrating the imaging tray with the vibrator to remove an overlap between the drugs corresponding to a dose supplied to the imaging tray and to correct the posture of the drugs using the first inclined surface and the second inclined surface of at least one of the V-shaped grooves;

an imaging step of capturing images of the drugs on the imaging tray illuminated by the light source, using the first camera and the second camera, to acquire a first image and a second image after the vibration step; and a drug information acquisition step of processing the first image and the second image acquired in the imaging step, using the drug information acquisition computer, to acquire drug information including at least outward appearance information of the drugs in the first image and the second image.

12. The drug information acquisition method according to claim 11, further comprising:

a storage step of storing in a memory, size correction information corresponding to an object distance of each V-shaped groove in the row of the V-shaped grooves in the bottom of the imaging tray, wherein the drug information acquisition step includes a reading step of reading the corresponding size correction information from the memory according to which of the V-shaped grooves in the row of the V-shaped grooves of the imaging tray the drug is located in, and a correcting step of correcting size information which is included in the outward appearance information acquired by the image processing with the read size correction information.

13. The drug information acquisition method according to claim 11, wherein in the drug information acquisition step, at least one of color information, character information, and a secant line of the drug in the image is further acquired by the image processing.

14. A drug information acquisition method that is performed in a drug information acquisition device including an imaging tray that is provided between a drug distribution tray and a packet insertion guide and has a bottom in which a row of V-shaped grooves, each having a first inclined surface and a second inclined surface, is formed, a vibrator that vibrates the imaging tray, light source that illuminates drugs on the imaging tray, a first camera and a second camera that are provided so as to face the first inclined surface and the second inclined surface in the bottom of the imaging tray, respectively, and a drug information acquisition computer, the method comprising:

a drug supply step of supplying each dose of a plurality of types of drugs from the drug distribution tray to the imaging tray;

a vibration step of vibrating the imaging tray with the vibrator to remove an overlap between the drugs corresponding to a dose supplied to the imaging tray and to correct the posture of the drugs using the first inclined surface and the second inclined surface of at least one of the V-shaped grooves;

a first imaging step of continuously capturing images of the drugs on the imaging tray illuminated by the illumination unit, using at least one of the first camera and the second camera, to acquire a continuous image during the vibration of the imaging tray in the vibration step;

a determination step of determining whether the overlap between the drugs corresponding to a dose supplied to the imaging tray has been removed and whether the posture of the drugs has been corrected, on the basis of the image acquired in the first imaging step;

a step of stopping the vibration of the imaging tray in the vibration step when it is determined in the determination step that the overlap between the drugs has been removed and the posture of the drugs has been corrected;

a second imaging step of capturing images of the drugs on the imaging tray illuminated by the light source, using the first camera and the second camera, to acquire a first image and a second image after the vibration of the imaging tray is stopped; and a drug information acquisition step of processing the first image and the second image acquired in the second imaging step, using the drug information acquisition computer, to acquire drug information including at least outward appearance information of the drugs in the first image and the second image.

15. The drug information acquisition method according to claim 14, further comprising:

a storage step of storing in a memory, size correction information corresponding to an object distance of each V-shaped groove in the row of the V-shaped grooves in the bottom of the imaging tray, wherein the drug information acquisition step includes a reading step of reading the corresponding size correction information from the memory according to which of the V-shaped grooves in the row of the V-shaped grooves of the imaging tray the drug is located in, and a correcting step of correcting size information which is included in the outward appearance information acquired by the image processing with the read size correction information.

16. The drug information acquisition method according to claim 14, wherein in the drug information acquisition step, at least one of color information, character information, and a secant line of the drug in the image is further acquired by the image processing.

* * * * *